(12) United States Patent
Takada

(10) Patent No.: US 8,262,562 B2
(45) Date of Patent: Sep. 11, 2012

(54) BENDING PORTION OF INSERTION PART OF ENDOSCOPE AND ENDOSCOPE PROVIDED WITH INSERTION PART INCLUDING BENDING PORTION

(75) Inventor: Tadatsugu Takada, Utsunomiya (JP)

(73) Assignee: Olympus Medical Systems Corp. (JP)

( * ) Notice: Subject to any disclaimer, the term of this patent is extended or adjusted under 35 U.S.C. 154(b) by 1280 days.

(21) Appl. No.: 11/936,886

(22) Filed: Nov. 8, 2007

(65) Prior Publication Data

US 2008/0294007 A1  Nov. 27, 2008

(30) Foreign Application Priority Data

Nov. 9, 2006 (JP) .................................. 2006-304396
Sep. 14, 2007 (JP) .................................. 2007-239899

(51) Int. Cl.
*A61B 1/00* (2006.01)
*F16L 9/00* (2006.01)

(52) U.S. Cl. ........ 600/139; 600/140; 600/141; 138/155; 604/523

(58) Field of Classification Search .................. 600/133, 600/128, 130, 136–142, 144; 604/523, 533–535
See application file for complete search history.

(56) References Cited

U.S. PATENT DOCUMENTS

| 4,347,837 | A * | 9/1982 | Hosono | 600/139 |
| 6,565,505 | B2 * | 5/2003 | Ishibiki | 600/133 |
| 2002/0026095 | A1 | 2/2002 | Sakamoto | |
| 2003/0191366 | A1 * | 10/2003 | Ishibiki | 600/133 |
| 2006/0258911 | A1 * | 11/2006 | Sato | 600/139 |

FOREIGN PATENT DOCUMENTS

| EP | 1 563 784 | 8/2005 |
| EP | 1 681 013 | 7/2006 |
| JP | 2000-166859 | 6/2000 |
| JP | 2002-125916 | 8/2002 |
| JP | 2004-166840 | 6/2004 |
| JP | 2005-287575 | 10/2005 |
| JP | 2006-122327 | 5/2006 |

OTHER PUBLICATIONS

European Search Report dated Mar. 14, 2008 corresponding to European Patent Application No. 07021812.8-2319.
Japanese Office Action dated Oct. 28, 2008 (with English translation of relevant portions).

* cited by examiner

*Primary Examiner* — Matthew J Kasztejna
*Assistant Examiner* — Ryan Henderson
(74) *Attorney, Agent, or Firm* — Ostrolenk Faber LLP

(57) ABSTRACT

An insertion part of an endoscope includes at least a bending portion and two portions connected to one and the other ends of the bending portion. A bending structure of the bending portion is connected at its other end adjoining area overlapping with an adjoining area of at least one of the two portions to the adjoining area of the at least one of the two portions by a fixing member. A thread member wound on an end portion of a flexible covering member covering the bending structure, the end portion corresponding to the fixing member, has a pulled-in part arranged between the outer peripheral surface of that end portion of the cover member and a winding portion formed by the wound thread member, and the pulled-in part is arranged in a side of the fixing member. The winding portion of the thread member is covered by a resin layer.

4 Claims, 13 Drawing Sheets

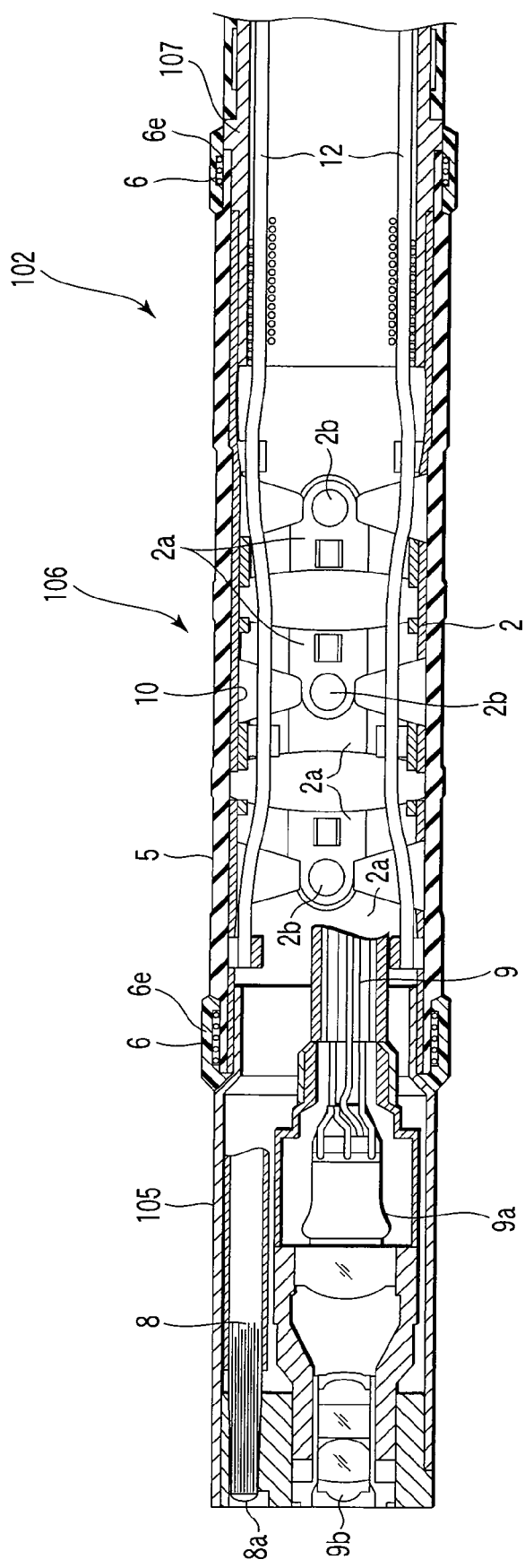
F I G. 1

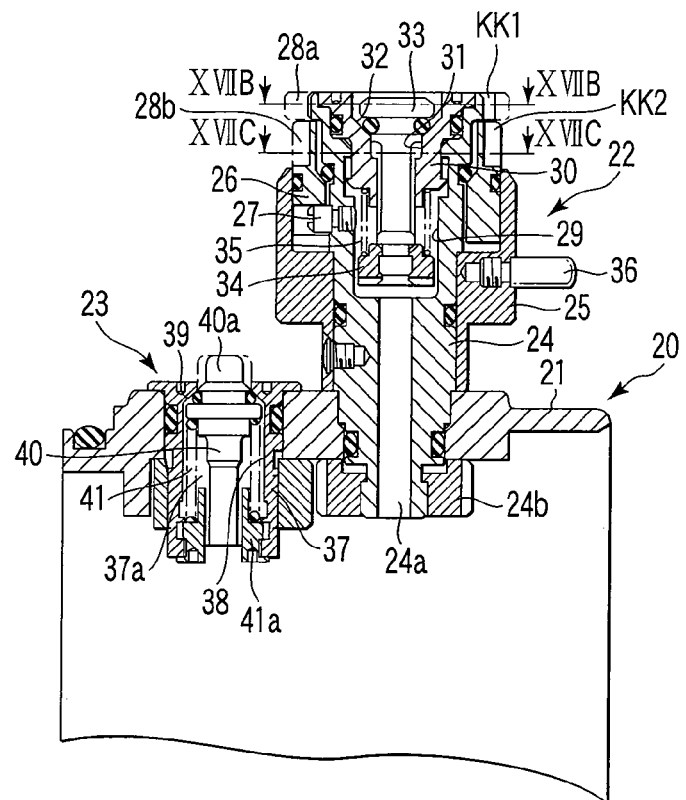
F I G. 17A
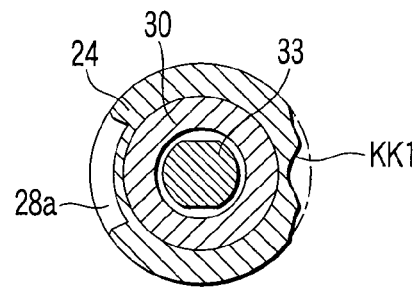
F I G. 17B
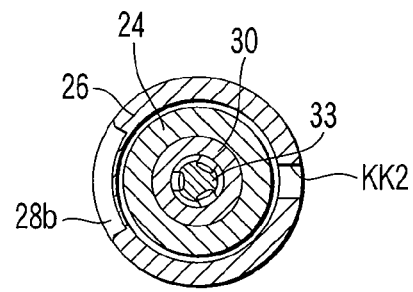
F I G. 17C

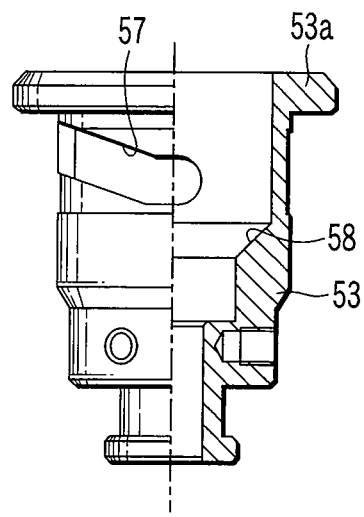
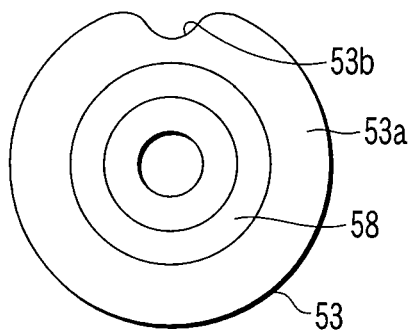
F I G. 20A    F I G. 20B
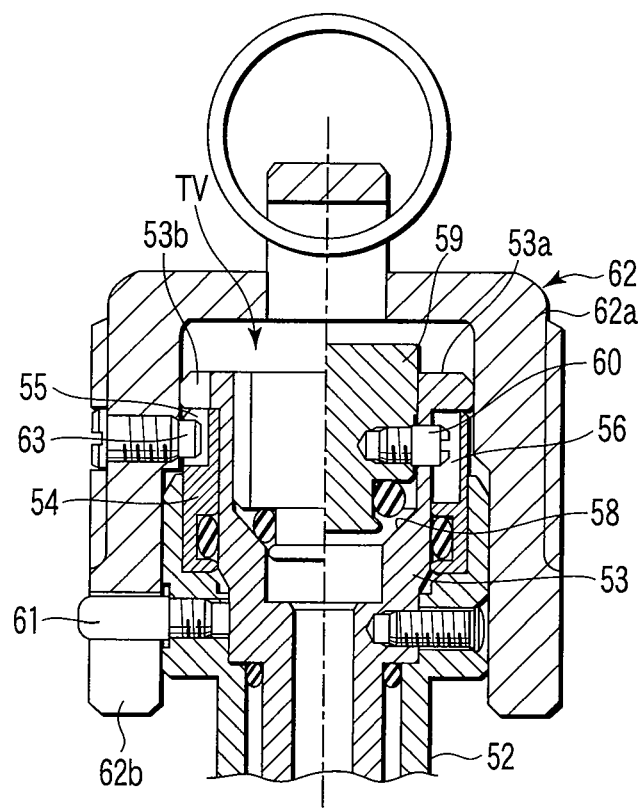
F I G. 21

BENDING PORTION OF INSERTION PART OF ENDOSCOPE AND ENDOSCOPE PROVIDED WITH INSERTION PART INCLUDING BENDING PORTION

CROSS-REFERENCE TO RELATED APPLICATIONS

This application is based upon and claims the benefit of priority from prior Japanese Patent Applications No. 2006-304396, filed Nov. 9, 2006; and No. 2007-239899, filed Sep. 14, 2007, the entire contents of both of which are incorporated herein by reference.

BACKGROUND OF THE INVENTION

1. Field of the Invention

The present invention relates to a bending portion of an insertion part of an endoscope and an endoscope provided with the insertion part including such a bending portion.

2. Description of the Related Art

The endoscope comprises: an elongate insertion part having a proximal end and a distal end and adapted to be inserted into an inner space of an object with the proximal end of the insertion part being as a head; and an operation part connected with the proximal end of the insertion part to operate the insertion part. The insertion part includes an insertion part main body extending from the proximal end to a neighborhood of the distal end, a bending portion having an end connected to the extending end of the insertion part main body, and a tip portion having a base end connected to the other end of the bending portion.

In a case of a flexible endoscope, the insertion part main body is called as a flexible portion which can flex only in a radius larger than a radius of the flexible bending portion when the bending portion is bent.

In a case of a medical endoscope, an object into which the insertion part of the endoscope is inserted is a living thing and an inner space of the object is a body cavity of the living thing.

The bending portion includes a bending structure having a plurality of annular members interconnected by a plurality of connecting pins to be bendable as a whole in four directions (cross directions). In the bending structure, for example, peripheral walls of the adjoining annular members are connected with each other by two coaxial connecting pins extending in two opposite directions (right and left directions, for example), so that the two adjoining annular members can bent in two opposite directions (up and down directions, for example) perpendicular to the aforementioned two opposite directions. Then, other annular members further adjoining the two adjoining annular members have a peripheral wall connected with the peripheral walls of the two adjoining annular members by two coaxial connecting pins extending in two opposite directions (the up and down directions, for example) perpendicular to the aforementioned two directions (the right and left directions, for example), and therefore, can be bent in the aforementioned two directions (the right and left directions, for example) with respect to the two adjoining annular members.

Four operating wires extending from the operation part through the insertion part main body are inserted in each of the annular members of the bending structure of the bending portion, and the four operating wires are arranged at four positions equidistantly apart from each other in a peripheral direction in each of the annular members. The distal ends of the four operating wires are fixed to the annular member adjoining the tip portion. The two operating wires are distant from each other in the two directions (the right and left directions, for example) in each of the annular members, and the proximal ends of the two operating wires are coupled to a first bending portion operating lever (a bending portion right and left operating lever, for example) arranged on the operation part. The remaining two operating wires are distant from each other in the other two directions (the up and down directions, for example) perpendicular to the aforementioned two directions (the right and left directions, for example) in each of the annular members, and the proximal ends of the remaining two operating wires are coupled to a second bending portion operating lever (a bending portion up and down operating lever, for example) arranged on the operation part.

By operating the first bending portion operating lever (the bending portion right and left operating lever, for example) of the operation part, the bending portion together with the tip portion can bent in the two directions (the right and left directions, for example) at the extending end of the insertion part main body of the insertion part of the endoscope. Also, by operating the second bending portion operating lever (the bending portion up and down operating lever, for example), the bending portion together with the tip portion can bend in the remaining two directions (the up and down directions, for example) perpendicular to the aforementioned two directions (the right and left directions, for example) at the extending end of the insertion part main body of the insertion part of the endoscope.

Various electric/electronic parts including an imaging device are accommodated in an inner space of the tip portion, and conductive lines extend from these electric/electronic parts to the operation part through the bending structure of the bending portion and the insertion part main body.

Further, in the insertion part, light guide members extend from the tip portion to the operation part through the bending structure of the bending portion and the insertion part main body.

On a tip end surface of the tip portion, an objective lens group is mounted in liquid-tight manner to face the imaging device and light projecting lens are mounted in liquid-tight manner to face tip ends of the light guide members.

The bending structure of the bending portion is covered by a braid which in turn is covered by a liquid-tight flexible cover member. Conventional cover member is made of rubber.

The cover member has one end portion and an other end portion, the one end portion covering on a base end area of an outer peripheral surface of the tip portion, and the other end portion covering a distal end area of an outer peripheral surface of the insertion part main body.

The one and other end portions of the cover member are fixed in liquid-tight state to the base end area of the outer peripheral surface of the tip portion and the distal end area of the outer peripheral surface of the insertion part main body by tightly winding a thread member a number of times on each of the outer peripheral surfaces of the one and other end portions of the cover member.

A thermosetting adhesive for preventing is applied to the winding portion of the thread member on the outer peripheral surface of each of the one and other end portions of the cover member to prevent the winding portion of the thread member from loosening.

The aforementioned fixing structures at the both end portions of the cover member on the bending portion of the insertion part of the endoscope is widely known as disclosed in, for example, Jpn. Pat. Appln. KOKAI Publication Nos. 2005-287575, 2000-166859 and 2004-166840.

Jpn. Pat. Appln. KOKAI Publication No. 2005-287575, for example, discloses an annular protrusion formed on an outer peripheral surface of one end portion of a cover member, and the annular protrusion is separated from one end surface of the one end portion. The annular protrusion clearly defines a range on which a thread member is tightly wound on the outer peripheral surface of the one end portion of the cover member after the one end portion of the cover member covers a coupling ring of an extending end of an insertion part main portion of an insertion part of an endoscope, to fix the one end portion of the cover member on the coupling ring in liquid-tight manner. At the same time, the annular protrusion prevents an adhesive which is applied to a winding portion of the thread member wound on the outer peripheral surface of the one end portion to prevent a loosening of the winding portion, from flowing out onto an outer peripheral surface of the remaining area of the cover member.

Jpn. Pat. Appln. KOKAI Publication No. 2000-166859 discloses that two end portions of the cover member are covered on an extending end area of an outer peripheral surface of an insertion part main body of an insertion part of an endoscope and on a base end area of an outer peripheral surface of an tip portion of the insertion part, and then thread members are wound tightly on the outer peripheral surfaces of the two end portions of the cover member to fix the two end portions of the cover member in liquid-tight manner on the extending end area of the outer peripheral surface of the insertion part main body of the insertion part and on the base end area of the outer peripheral surface of the tip portion of the insertion part, and then an adhesive is applied to the winding portion of the thread member on each of the both end portions of the cover member to prevent the winding portion from loosening, and finally a heat-shrinkable tube covers the adhesive.

Jpn. Pat. Appln. KOKAI Publication No. 2004-166840 discloses that two end portions of a cover member are covered on an extending end area on an outer peripheral surface of an insertion part main body of an insertion part of an endoscope and a base end area of an outer peripheral surface of a tip portion of the insertion part, and then thread members are wound tightly on the outer peripheral surfaces of the two end portions of the cover member to fix the two end portions of the cover member in liquid-tight manner on the extending end area of the outer peripheral surface of the insertion part main body of the insertion part and on the base end area of the outer peripheral surface of the tip portion of the insertion part, and finally an adhesive is applied to the winding portion of the thread member on each of the both end portions of the cover member to prevent the winding portion from loosening. The thread member is wound with a predetermined force on the outer peripheral surface of each of the two end portions of the cover member in such a manner that a thickness of each of the two end portions on which the thread members are wound is 40% to 95% of the thickness of each of the two end portions in a natural state in which the thread members are not wound on the two end portions.

In each of the conventional fixing structures for the both end portions of the cover member covering the bending portion of the insertion part of the endoscope, winding start and winding end portions of the thread member wound on the outer peripheral surface of each of the two end portions of the cover member are temporally fixed on each of the two end portions before applying the adhesive thereto as described below. Specifically, at first the winding start portion of the thread member is extended in a longitudinal direction of the cover member on each of the outer peripheral surfaces of the two end portions before the thread member is wound on each of the outer peripheral surfaces of the two end portions of the cover member, and the winding start portion of the thread member is pressed on each of the outer peripheral surfaces by winding the thread member on each of the outer peripheral surfaces of the two end portions. The winding end portion of the thread member is pulled in between the winding portion of the thread member formed on each of the outer peripheral surfaces of the two end portions of the cover member and each of the outer peripheral surfaces of the two end portions of the cover member, and thus extended in the longitudinal direction of the cover member.

Next, with reference to FIGS. 22 and 23, a typical example of the conventional fixing structure for fixing one end portion of the cover member on the base end area of the tip portion in the bending portion of the insertion part of the endoscope, will be explained.

A bending structure 2 of the bending portion 106 of the insertion part of the endoscope has a plurality of annular members 2a interconnected by a plurality of connecting pins 2b to be bendable as a whole for example in four directions (cross directions).

An intermediate portion of an outer peripheral surface of the bending structure 2 between the both end portions thereof is covered by a braid 10 knitted by thin metal wire or synthetic fiber into a tube.

In the bending structure 2 of the bending portion 106 of the insertion part of the endoscope, the other-end area including the other end connected to a base end of a tip portion 105 located at a position opposite to an extending end of an insertion part main body which is not shown, overlaps with a base-end area of the tip portion 105 including the base end thereof. The other end area of the bending structure 2 is fixed to the base-end area of the tip portion 105 by a plurality of fixing members 4. The conventional fixing member 4 is a headed screw.

The bending structure 2 of the bending portion 106 is covered by a flexible cover member 5 from not shown one end to the other end thereof. The conventional cover member 5 is formed of rubber. A thread member 6 is wound spirally on each of the outer peripheral surfaces of one and the other end portions of the cover member 5 and thus makes up a winding portion, the one end portion of the cover member 5 corresponding to the one-end area (overlapped with the extending end area of the not shown insertion part main body) of the bending structure 2, and the other end portion of the cover member 5 corresponding to the other end area (overlapped with the base end area of the tip end portion 3) of the bending structure 2.

Conventionally, the thread member 6 is wound on the outer peripheral surface of each of the one and other end portions of the cover member 5 in a manner described below.

At first, a portion of the thread member 6 in the neighborhood of a winding start portion 6b thereof is wound on each of the outer peripheral surfaces of the one and other end portions of the cover member 5 to form a knot 6a, and then the winding start portion 6b is extended along the longitudinal center line of the bending structure 2 on each of the outer peripheral surfaces. Next, the thread member 6 is spirally and tightly wound in a direction of an arrow in FIG. 22 on each of the outer peripheral surfaces to form a winding portion 6c and to make the winding start portion 6b is pressed on each of the outer peripheral surfaces by the winding portion 6c. A winding end portion 6d of the thread member 6 remaining after forming the winding portion 6c is pulled in between the winding portion 6c and each of the outer peripheral surface, so that the winding end portion 6d is temporarily fixed.

The winding start portion 6b of the thread member 6 and the winding end portion 6d thereof are extended substantially parallel to each other along the longitudinal center line of the bending structure 2 between each of the outer peripheral surfaces and the winding portion 6c.

Each head 4a of the fixing members 4 fixing the other end area of the bending structure 2 to the base end area of the tip portion 105 while the other end area and the base end area are overlapping with each other generates an unevenness on the outer peripheral surface of the radially outer one of the other end area of the bending structure 2 and the base end area of the tip portion 105. As used herein, the term "radially side one" means one of i) the other end area of the bending structure 2 and ii) the base end area of the tip portion 105, the one being radially located outside of the other.

In FIGS. 22 and 23, the radially outer one is the other end area of the bending structure 2. After fixing the other end area of the bending structure 2 to the base end area of the tip portion 3, each head 4a of the fixing members 4 is machined to conform with the outer peripheral surface of the above described radially outer one. Nevertheless, it has been difficult to eliminate the unevenness completely.

The winding portion 6c of the thread member 6 is coated with a resin layer 6e of, for example, a thermosetting adhesive and covered by the resin layer 6e to prevent the winding portion 6c from loosening.

An endoscope used in a medical field must be sterilized after it is used. Various methods for sterilization are known. In a case where a sterilization method using an autoclave device is employed, a problem described below is liable to occur.

The endoscope to be sterilized is placed in the autoclave device and heated to a high temperature (about 135° C.) under high pressure by the autoclave device. In this time, the cover member 5 made of rubber is softened and decreased in its diameter.

In the case where the unevenness is generated on the outer peripheral surface of the radially outer one of the other end adjoining area of the bending structure 2 and the base end area of the tip portion 105 (in FIGS. 22 and 23, the radially outer one is the other end area of the bending structure 2), a change in stress distribution is generated at the boundary of the unevenness in the portion of the resin layer 6e corresponding to the unevenness through the cover member 5 during the sterilization using the autoclave device.

The thickness of a portion of the resin layer 6e corresponding to each of the winding start portion 6b and the winding end portion 6d of the thread member 6 wound on each outer peripheral surface of the one and other end portions of the cover member 5 is smaller than the thickness of the remaining portion of the resin layer 6e.

In a case where at least one of the winding start portion 6b and the winding end portion 6d of the thread member 6 is overlapped with at least one of the heads 4a of the plural fixing member 4 as shown in FIGS. 22 and 23, therefore, the thin portion of the resin layer 6e (i.e. the portion of the resin layer 6e corresponding, through the cover member 5, to the aforementioned unevenness developed by the head 4a of the fixing members 4) corresponding to the at least one of the winding start portion 6b and the winding end portion 6d of the thread member 6 of the resin layer 6e is liable to crack due to the change in stress distribution caused by the remaining thick portion of the resin layer 6e during the sterilization using the autoclave device.

The cracking loosens the winding portion 6c of the thread member 6 wound on the cover member 5, and therefore, the liquid tightness provided by the cover member 5 may be disrupted.

FIGS. 22 and 23 further show light guide members 8 extending from the operation part not shown, through the bending structure 2 of the bending portion 106 and the insertion part main body not shown, to the tip portion 3. FIGS. 22 and 23 further show a plurality of conductive lines 9 extending to the operation part not shown, through the bending structure 2 and the insertion part main body not shown, from the various electric/electronic parts including the imaging device accommodated in the inner space of the tip portion 3.

BRIEF SUMMARY OF THE INVENTION

A bending portion of an elongate insertion part of an endoscope, the endoscope including an operation part configured for operating the elongate insertion part, the elongate insertion part including a proximal end and a distal end and adapted to be inserted into an inner space of an object, with the distal end as a leading end, and the operation part of the endoscope being connected to the proximal end of the elongate insertion part, and the elongate insertion part including an insertion part main body which has the proximal end, which extends toward the distal end and which has an extending end area proximate to the distal end, a tip portion which has the distal end and which has a base end area proximate to the extending end area of the insertion part main body, and a bending portion which is arranged between the extending end area of the insertion part main body and the base end area of the tip portion and which has one end area connected to the extending end area of the insertion main body and the other end area connected to the base end area of the tip portion, and the bending portion together with the tip portion being bendable by being operated with the operation part, the bending portion comprising:

a bending structure including first and second portions which correspond to the one end area and the other end area of the bending portion, the first portion and second portion overlapping the extending end area of the insertion part main body and the base end area of the tip portion;

a first fixing member fixing the first portion of the bending structure to the extending end area of the insertion part main body overlapped with the first portion, and having a head exposing on an outer surface of the first portion;

a second fixing member fixing the second portion of the bending structure to the base end area of the tip portion overlapped with the second portion, and having a head exposing on an outer surface of the second portion;

a flexible cover member which covers the bending structure from the first portion to the second portion, which also covers the heads of the first and second fixing members, and which has one end and the other end portion corresponding to the first and second portion of the bending structure;

thread members wound on the one and the other end portions of the covering member, and making up winding portions on the one and the other end portions; and resin layers covering the winding portions of the thread members wound on the one and the other end portions of the cover member, wherein the thread member has a winding start portion and a winding end portion both which are arranged between each of the one and the other end portions of the cover member and the winding portion thereon, both of which extend in a longitudinal direction of the insertion part, and the winding start portion and winding end portion of the thread member wound on each of the one and the other end portions of the cover member are separated from the head of the fixing member corresponding thereto in a circumferential direction of each of the one and the other end portion of the cover member and are separated from each other in the circumferential direction.

The thread member making up the winding portion on the outer peripheral surface of each of the one and the other end portions of the cover member has a pulled-in part arranged between the outer peripheral surface of each of the one and the other end portions of the cover member and the winding portion thereon, and the pulled-in part of the thread member wound on the outer peripheral surface of the at least one of the one and the other end portions of the cover member, the at least one corresponding to the fixing member, is arranged in a side of the fixing member.

An endoscope, according to one aspect of the present invention, comprises:

an elongate insertion part adapted to be inserted into an inner space of an object; and an operation part connected to a proximal end of the insertion part and operating the insertion part, the insertion part including at least a bending portion and two portions connected to one and the other ends of the bending portion, the bending portion comprising:

a bending structure including a one-end adjoining area having the one end and an other-end adjoining area having the other end, configured to be bendable, and at least one of the one-end adjoining area and the other-end adjoining area being overlapped with an adjoining area of at least one of the two portions corresponding thereto;

a fixing member fixing the at least one of the one-end adjoining area and the other-end adjoining area in the bending structure to the adjoining area of the at least one of the two portions corresponding thereto;

a flexible cover member which covers the bending structure from the one end to the other end;

thread members wound on outer peripheral surfaces of one and the other end portions of the covering member, the one and the other end portions corresponding to the one-end and the other-end adjoining areas of the bending structure, and making up winding portions on the one and the other end portions; and resin layers covering the winding portions of the thread members wound on the outer peripheral surfaces of the one and the other end portions of the cover member.

The thread member making up the winding portion on the outer peripheral surface of each of the one and the other end portions of the cover member has a pulled-in part arranged between the outer peripheral surface of each of the one and the other end portions of the cover member and the winding portion thereon, and the pulled-in part of the thread member wound on the outer peripheral surface of the at least one of the one and the other end portions of the cover member, the at least one corresponding to the fixing member, is arranged in a side of the fixing member.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic longitudinal sectional view of an area in the neighborhood of a distal end of an insertion part of an endoscope, the area in the neighborhood of the distal end of the insertion part including an extending end of an insertion part main body, a bending portion according to a first embodiment of the invention, and a tip portion of the insertion part;

FIG. 17A is a schematic longitudinal sectional view of a check valve device and a vent valve device in an endoscope which can be sterilized by an autoclave device and which is according to another embodiment of the present invention;

FIG. 17B is a schematic horizontal sectional view taken along a line XVIIB-XVIIB in FIG. 17A;

FIG. 17C is a schematic horizontal sectional view taken along a line XVIIC-XVIIC in FIG. 17A;

FIG. 20A is a half sectional view of an inner cylindrical member of the vent valve device shown in FIG. 19;

FIG. 20B is a top view of the inner cylindrical member shown in FIG. 20A;

FIG. 21 is a longitudinal sectional view schematically showing a cap for gas sterilization used for the vent valve device of FIG. 19, the cap for gas sterilization being mounted on the vent valve device, in the left half of which a vent valve member is arranged in its closed position and in the right half of which the vent valve member is arranged in its opening position;

DETAILED DESCRIPTION OF THE INVENTION

Now, bending portions of insertion parts of endoscopes and endoscopes comprising such the bending portions, according to various embodiments of the present invention, will be explained below with reference to the drawings.

Figure 2:
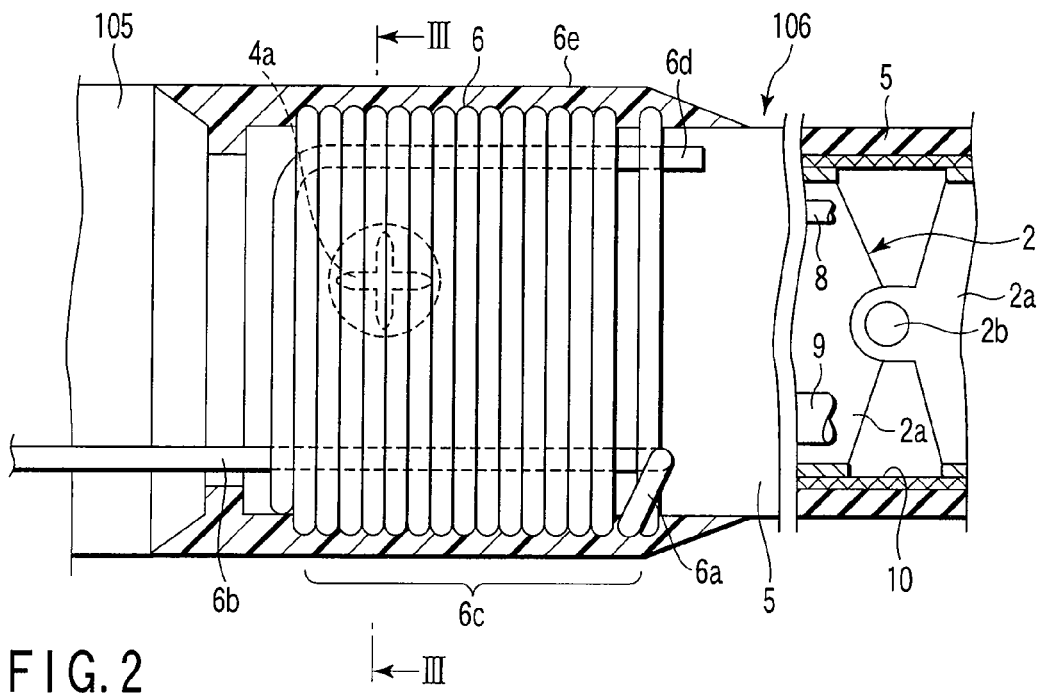
FIG. 2 is a schematic side view of an area in which the other end of the bending portion and a base end of the tip portion in FIG. 1 are connected to each other, with only a resin layer located at the radially outermost position in the area being cross sectioned.
Figure 3:
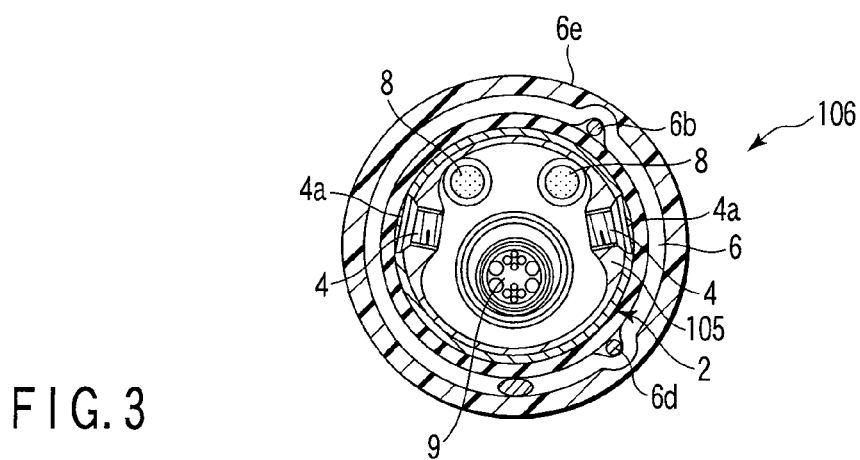
FIG. 3 is a schematic cross sectional view taken along a line III-III in FIG. 2.
Figure 22:
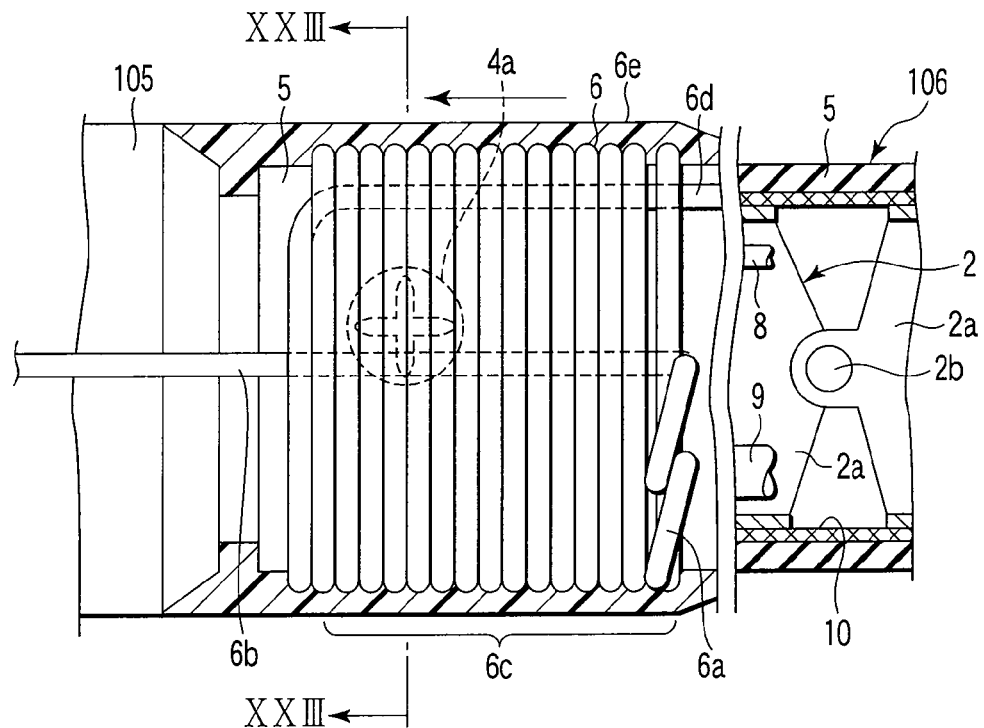
FIG. 22 is a side view schematically showing an area in which the other end of a bending portion and a base end of a tip portion in an insertion part of the conventional endoscope are connected to each other, with only a resin layer located at the radially outermost position in the area being cut away, and with a schematic longitudinal sectional view of a part of the bending portion in the neighborhood of that area.
Figure 23:
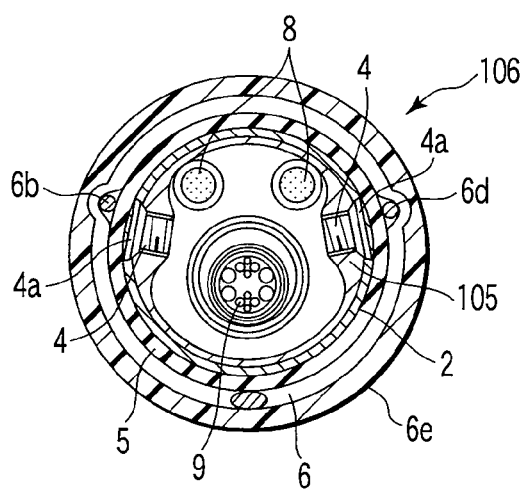
FIG. 23 is a schematic sectional view taken along a line XXIII-XXIII in FIG. 22.

In a bending portion of an insertion part of an endoscope, according to a first embodiment of the present invention and shown in FIGS. 1 to 3, components which are the same as those of the bending portion of the insertion part of the conventional endoscope shown in FIGS. 22 and 23 are designated by the same reference numerals as those designating the conventional same components, and detailed descriptions about these components will be omitted.

The endoscope comprises an elongate insertion part 102 having a proximal end and a distal end and adapted to be inserted into an inner space of an object with the proximal end of the insertion part being as a head, and an operation part connected with the proximal end of the insertion part 102 to operate the insertion part 102. The insertion part 102 includes an insertion part main body 107 extending from the proximal end to a neighborhood of the distal end, a bending portion 106 having an end connected to the extending end of the insertion part main body 107, and a tip portion 105 having a base end connected to the other end of the bending portion 106. The insertion part main body 107 may be configured to be flexible or may be configured to be substantially un-flexible.

Specifically, the bending portion 106 included in the insertion part 102 of the endoscope comprises a bending structure 2 includes a plurality of annular members 2a interconnected by a plurality of connecting pins 2b to be bendable as a whole for example in four directions (cross directions).

The bending portion 106 further comprises a braid 10 formed by knitting thin metal wires or chemical fibers into a cylindrical shape and covering an outer peripheral surface of the bending structure 2. Both end portions of the braid 10 are fixed to the annular members 2a arranged at the both end portions of the bending structure 2 by a conventional fixing element including an adhesive, solder, or the like.

The other end area of the bending structure 2, adjoining the tip portion 105, and the base end area of the tip portion 105 are overlapped with each other, and are fixed with each other by a fixing member 4 passing through them and being preferably a plurality of headed screws.

Also, one end area of the bending structure 2, adjoining the insertion part main body 107, and the extending end area of the insertion part main body 107, adjoining the bending portion 6, are overlapped with each other, and are fixed with each other by a fixing member passing through them and being preferably a plurality of headed screws.

In FIG. 1, two of the four operating wires 12 are shown. These operating wires 12 extend from the first bending portion operating lever (the bending portion right and left operating lever, for example) and the second bending portion operating lever (the bending portion up and down operating lever, for example) on the not shown operation part of the endoscope through the insertion part main body 107 into the inner space of the plurality of the annular members 2a of the bending structure 2 of the bending portion 106 so as to operate a bending of the bending portion 106. FIG. 1 further shows that the distal ends of the two of the four operating wires 12 are fixed to the annular member 2a adjoining the tip portion 105.

FIG. 1 further shows the extending ends of the light guide members 8 and the various electric/electronic parts including the imaging device 9a connected to the extending ends of the conductive lines 9, which are accommodated in the inner space of the tip portion 105. Further, FIG. 1 shows the objective lens group 9b mounted in liquid-tight manner on the tip end surface of the tip portion 105 to face the imaging device 9a, and the light projecting lens 8a mounted in liquid-tight manner on the tip end surface of the tip portion 105 to face the tip ends of the light guide members 8.

The bending structure 2 with the braid 10 is covered by the flexible cover member 5 from its one end located in a side of the insertion part main body 107 and to it's the other end located in a side of the tip portion 105.

The one and the other end portions of the cover member 5 correspond to the one end area (overlapping with the extending end area of the insertion part main body 107) and other end area (overlapping with the base end area of the tip portion 105) of the bending structure 2, and the thread member 6 is wound spirally on the outer peripheral surface of each of the one and the other end portions of the cover member 5 and makes the winding portion 6c.

The winding of the thread member 6 on the outer peripheral surface of each of the one and the other end portions of the cover member 5 is performed in the same manner as in the conventional case described above with reference to FIGS. 22 and 23. However, the relative position of each of the winding start portion 6b and winding end portion 6d as the pulled-in part of the thread member 6 between the winding portion 6c and the above described outer peripheral surface with respect to the fixing member 4 is different from that in the conventional case described above.

That is, as apparent from FIGS. 2 and 3, the winding start portion 6b and winding end portion 6d of the thread member 6 are arranged on the outer peripheral surface of each of the one and the other end portions of the cover member 5 to separate from the fixing member 4 corresponding thereto in its side, specifically in the circumferential direction of the outer peripheral surface.

In this embodiment, the thread member 6 is configured by a fiber having a high strength and a high modulus of elasticity such as Kevlar (registered trademark) fiber. However, the thread member 6 may be configured by a thermoplastic resin monofilament of polyolefin group such as polypropylene or polyethylene.

Also, the resin layer 6e covering the winding portion 6c of the thread member 6 is preferably formed by a plurality of layers of thermosetting resin stacked one by one.

The thermosetting resin forming the resin layer 6e is a two-part adhesive as disclosed in Jpn. Pat. Appln. KOKAI Publication No. 2006-216102, the two-part adhesive formed by mixing a base of at least one of epoxy resin of bisphenol A and epoxy resin of bisphenol F in which acrylic rubber particles having average particle size of 300 nm or less are contained in the amount of 5 to 15 weight of the at least one epoxy resin with a curing agent the main components of which are dimer acid, diethylenetriamine and diethylenetriamine monomer. Nevertheless, any thermosetting resin may be used.

In the bending portion 106 of the insertion part 102 of the endoscope, according to the embodiment, each of the winding start portion 6b and the winding end portion 6d configuring the pulled-in part of the thread member 6 located between the outer peripheral surface of each of the one and the other end portions of the cover member 5 and the winding portion 6c of the thread member 6 wound on each outer peripheral surface is separated from the fixing member 4 corresponding thereto on the outer peripheral surface of each of the one and the other end portions of the cover member 5 in a side of the corresponding fixing member 4, specifically in the circumferential direction of the outer peripheral surface. And, in this embodiment, the winding start portion 6b and the winding end portion 6d of the thread member 6 extend in parallel to the longitudinal center line of the bending portion 106 with the corresponding head 4a of the fixing member 4 being arranged therebetween.

Therefore, the thin portions in the resin layer 6e covering the winding portion 6c of the thread 6 on the outer peripheral surface of each of the one and the other end portions of the cover member 5, the thin portions corresponding to the winding start portion 6b and winding end portion 6d of the thread 6, do not overlap with the unevenness portion of each of the one and the other end portions of the cover member 5, the unevenness portion corresponding to the head 4a of the fixing member 4.

As a result, even if the endoscope comprising the insertion part 102 including the bending portion 106 according to this embodiment is heated in the pressurized condition by a pressuring and heating device such as an autoclave device and the change in the stress distribution is generated in the portion of the resin layer 6e corresponding to the unevenness portion of each of the one and the other end portions of the cover member 5, the portions of the resin layer 6e corresponding to the unevenness portions of each of the one and the other end portions of the cover member 5 are hard to be cracked. This prevent the winding portion 6c of the thread member 6 on the outer peripheral surface of each of the one and the other end portions of the cover member 5, the winding portion 6c being covered with the resin layer 6e, from loosing, and thus the break of the liquid tightness of any of the one and the other end portions of the cover member 5 will be hard to occur.

Figure 4:
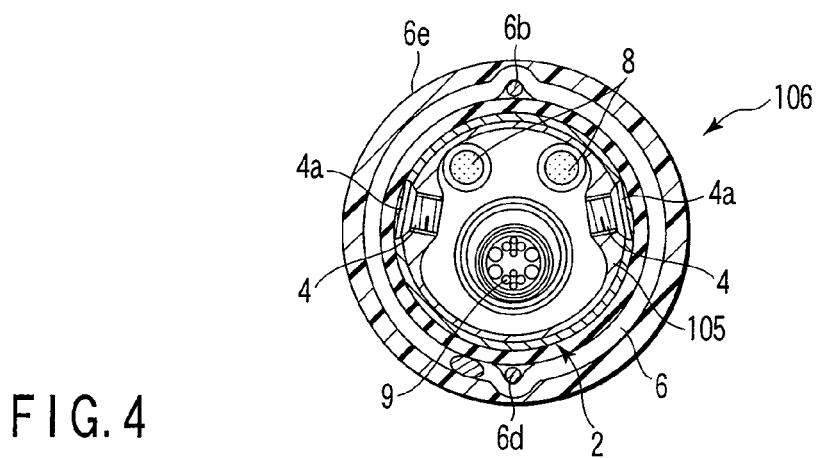
FIG. 4 is a schematic cross sectional view similar to FIG. 3, showing a bending portion of the insertion part of the endoscope, the bending portion according to a second embodiment of the invention.

In FIG. 4, a schematic cross sectional view of the bending portion 106 of the insertion part of the endoscope, according to a second embodiment of the present invention, is shown. Most configuration of the bending portion 106 of the insertion part of the endoscope, according to a second embodiment of the present invention, is the same as that of the bending portion 106 of the insertion part of the endoscope, according to the first embodiment of the present invention and described above with reference to FIGS. 1 to 3.

The configuration of the bending portion 106 of the insertion part of the endoscope, according to the second embodiment of the present invention and shown in FIG. 4, is different from that of the bending portion 106 of the insertion part of the endoscope, according to the first embodiment of the present invention and described above with reference to FIGS. 1 to 3 as follows. That is, the winding start portion 6b and winding end portion 6d of the pulled-in part of the thread member 6, located between the outer peripheral surface of each of the one and the other end portions of the cover member 5 and the winding portion 6c of the thread member 6 wound on the outer peripheral surface, are separated from the fixing member 4 corresponding thereto on the outer peripheral surface of each of the one and the other end portions of the cover member 5 in its sides, specifically in the circumferential direction of the outer peripheral surface by 180 degrees from each other. This means that the winding start portion 6b and winding end portion 6d of the pulled-in part of the thread member 6 are separated from each other in the diametrical direction relative to the longitudinal center line of the bending portion 106, and the corresponding head 4a of the fixing screw 4 is arranged at the middle position between the winding start portion 6b and winding end portion 6d of the pulled-in part of the thread member 6 in the circumferential direction of the cover member 5. In this embodiment, the winding start portion 6b and winding end portion 6d of the thread member 6 extend in parallel to each other with respect to the longitudinal center line of the bending portion 106.

With such a configuration, the thin portions in the resin layer 6e covering the winding portion 6e of the thread 6 on the outer peripheral surface of each of the one and the other end portions of the cover member 5, the thin portions corresponding to the winding start portion 6b and winding end portion 6d of the thread 6, are most separated from the unevenness portion of each of the one and the other end portions of the cover member 5, the unevenness portion corresponding to the head 4a of the fixing member 4.

As a result, even if the endoscope comprising the insertion part 102 including the bending portion 106 according to this embodiment is heated in the pressuring condition by a pressurizing and heating device such as an autoclave device and the change in the stress distribution is generated in the portion of the resin layer 6e corresponding to the unevenness portion of each of the one and the other end portions of the cover member 5, the portions of the resin layer 6e corresponding to the unevenness portions of each of the one and the other end portions of the cover member 5 are more hard to be cracked in comparison with the case of the first embodiment described above. This more prevent the winding portion 6c of the thread member 6 on the outer peripheral surface of each of the one and the other end portions of the cover member 5, the winding portion 6c being covered with the resin layer 6e, from loosing in comparison with the case of the first embodiment described above, and thus the break of the liquid tightness of any of the one and the other end portions of the cover member 5 will be more hard to occur.

Next, a whole configuration of the endoscope 101 of the according to the embodiment of the present invention and comprising the insertion part 102 including the bending portion 106 according to the first or second embodiment of the present invention and shown in FIGS. 1 to 4, will be explained with reference to FIGS. 5 to 10.

Figure 5:
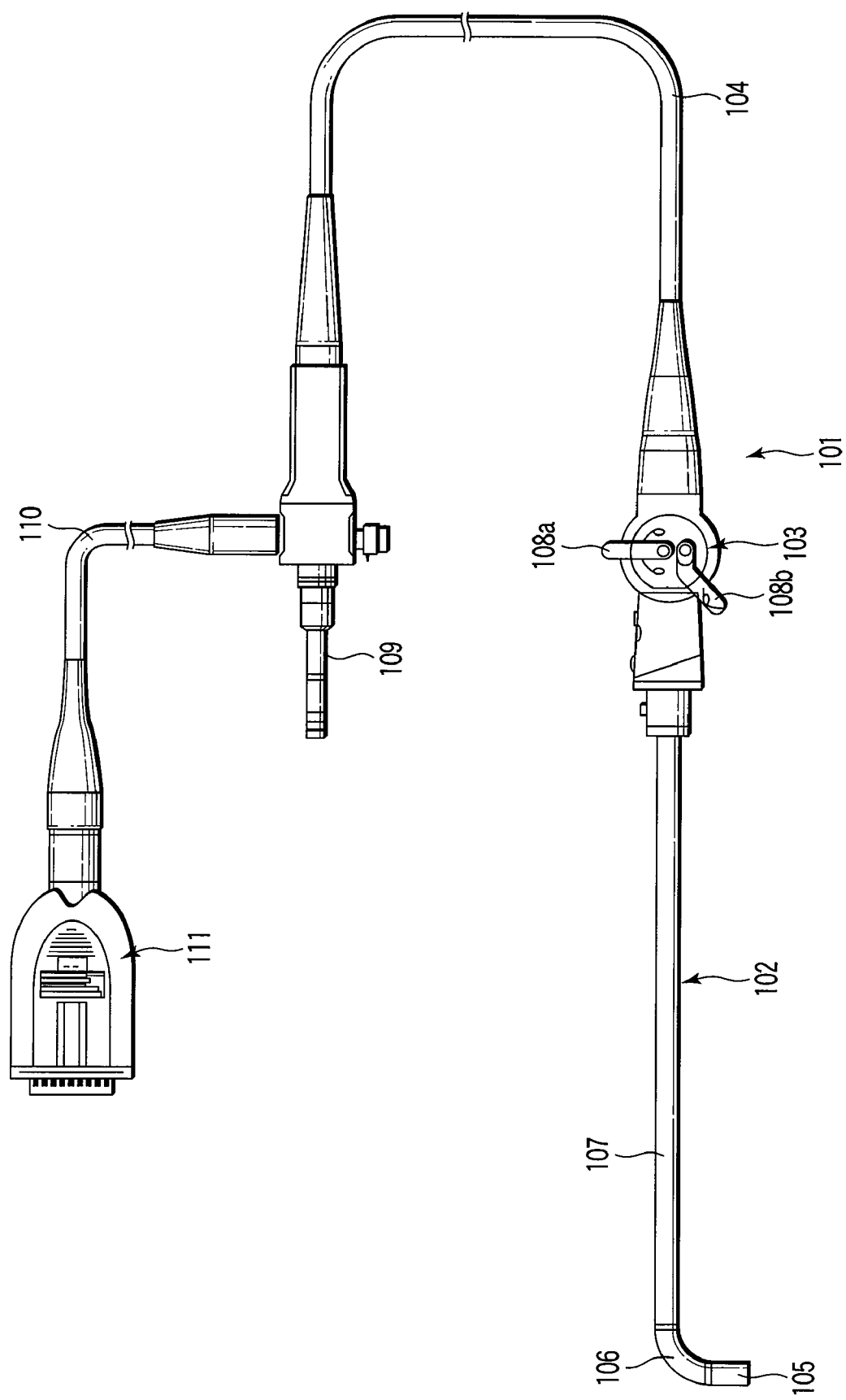
FIG. 5 is a drawing schematically showing the whole of an electronic endoscope according to an embodiment of the present invention and being provided with an insertion part including the bending portion according to the first or the second embodiment of the present invention shown in FIGS. 1 to 4.

In FIG. 5, the elongate insertion part 102 having the proximal end and the distal end and adapted to be inserted into the inner space of the object with the proximal end of the insertion part being as a head, and the operation part 103 connected with the proximal end of the insertion part 102 to operate the insertion part 102, the elongate insertion part 102 and the operation part 103 being provided in the endoscope 101, are shown. FIG. 5 further shows the insertion part main body 107 extending from the proximal end to the neighborhood of the distal end, the bending portion 106 having the end connected to the extending end of the insertion part main body 107, and the tip portion 105 having the base end connected to the other end of the bending portion 106, the insertion part main body 107, the bending portion 106, and the tip portion 105 being included in the insertion part 102.

FIG. 5 further shows the first bending portion operating lever (the bending portion right and left operating lever, for example) 108a and the second bending portion operating lever (the bending portion up and down operating lever, for example) 108b, the first and second levers 108a, 108b being swingably mounted on the operation part 103. The first bending portion operating lever (the bending portion right and left operating lever, for example) 108a and the second bending portion operating lever (the bending portion up and down operating lever, for example) 108b are connected to the proximal ends of the four operating wires 12 (only the two of the four operating wires 12 are shown in FIG. 1) extending from the operation part 103 into the inner space of the plurality of the annular members 2a of the bending structure 2 of the bending portion 106 so as to operate the bending of the bending portion 106 with the tip portion 105 in the four directions (cross directions).

The endoscope 101 further has a flexible universal cord 104 extending from the operation part 103 in a direction opposite to the insertion part 102. In the universal cord 104, the light guide members 8 and conductive lines 9 described above and with reference to FIG. 1 and extending from the tip portion 105 of the insertion part 102 to the operation part 103 through the bending portion 106 and the insertion part main body 107 further extend.

A light guide connector 109 is provided on the extending end portion of the universal cord 104, and the light guide connector 109 can connect the proximal ends of the light guide members 8 to a not shown outer light source. A camera cable 110 is branched from the extending end portion of the universal cord 104, and the camera cable 110 includes signal lines 115 connected the conductive lines 9. A connector 111 for electrically connecting with a CCU (Camera Control Unit) is provided on the extending end portion of the camera cable 110. The CCU is for example a control device and signal processing device which is used to control the operations of the various electric and/or electronics parts including the imaging device 9a (referring to FIG. 1) accommodated in the tip portion 105 of the insertion part 102 and to process the signals from the various electric and/or electronics parts.

Figure 6:
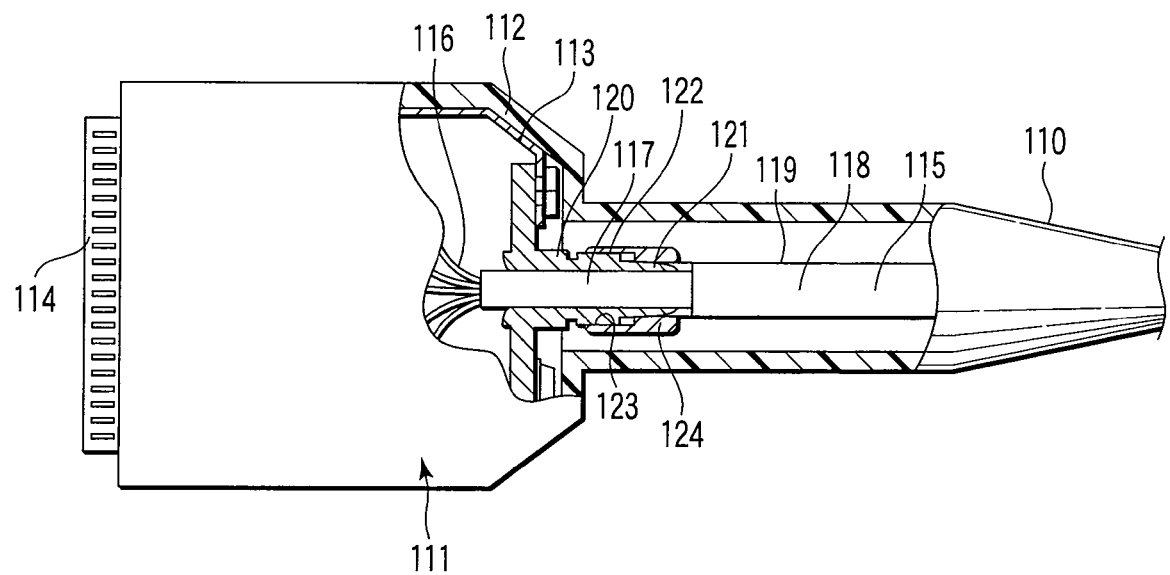
FIG. 6 is a side view schematically showing a connector for a camera control unit, branching from a universal cord extending from an operation part of the electronic endoscope shown in FIG. 5, a part of the connector being cut.

Next, the configuration of the connector 111 for the CCU will be explained with reference to FIG. 6. The CCU connector 111 includes an outer case 112, a sealing case 113 mounted in an inner side of the outer case 112 and electrically connected to a patient ground of the CCU, and an electrical contact portion 114 mounted on an end surface of the outer case 112.

In an inner space of the CCU connector 111, the proximal end of a signal line 115 connected to the conductive lines 9 from the imaging device 9a (referring to FIG. 1) accommodated in the tip portion 105 of the insertion part 102 are accommodated. The signal line 115 includes core lines 116 arranged in its center, a general seal 117 out fitted on the core lines 116 and configured by for example a metal braid, and an insulating outer cover 119 out fitted on the general seal 117. A seal member 119 for sealing electromagnetic waves is further fitted on the signal line 115, and the seal member 119 is configured by for example a metal braid.

A connection member 120 of an electrically conductive material is electrically and mechanically connected to a base end of the sealing case 113. The connection member 120 has a projection projecting into the camera cable 110, and a through hole is formed in the center of the projection. The through hole has an inner diameter into which the general seal 117 at the proximal end of the signal line 115. The general seal 117 inserted into the through hole of the connection member 120 is connected to the connection member 120 by a well known electrically and mechanically fixing element such as solder or the like.

A projecting side of an outer peripheral surface of the projection of the connection member 120 is shaped as a taper portion 121 having a taper shape decreasing its diameter with approaching to the projecting end of the projection, and a base end side of the outer peripheral surface of the projection is shaped as a male screw portion 122. On the taper portion 121, a portion of the seal member 119 located in the proximal end of the signal line 115 is fitted. The portion of the seal member 119 was once covering a portion of the general seal 117 located in the proximal end of the signal line 115 and was removed from the portion of the general seal 117 when the portion of the general seal 117 was inserted in the through hole of the projection of the connection member 120. That is, that portion of the general seal 117 is a removed portion.

On the removed portion of the seal member 119 fitted on the outer peripheral surface of the projection of the connection member 120, a taper tube 124 is fitted. The inner peripheral surface of the taper tube 124 is configured to have a taper shape which is parallel to the taper portion 121 of the outer peripheral surface of the projection of the connection member 120, and a female screw portion 123 is further formed on the inner peripheral surface. The female screw portion 123 is configured to screw on the male screw portion 122 in the base end side on the outer peripheral surface of projection of the connection member 120. And, by screwing female screw portion 123 of the inner peripheral surface of the taper tube 124 on the male screw portion 122 in the base end side on the outer peripheral surface of projection of the connection member 12, the removed portion of the seal member 119 in the proximal end of the conductive line 9 is pressed on the taper portion 121 in the projecting end side on the outer peripheral surface of the projection of the connection member 120 by the taper shaped inner peripheral surface of the taper tube 124, and is electrically and mechanically connected thereto.

Figure 7:
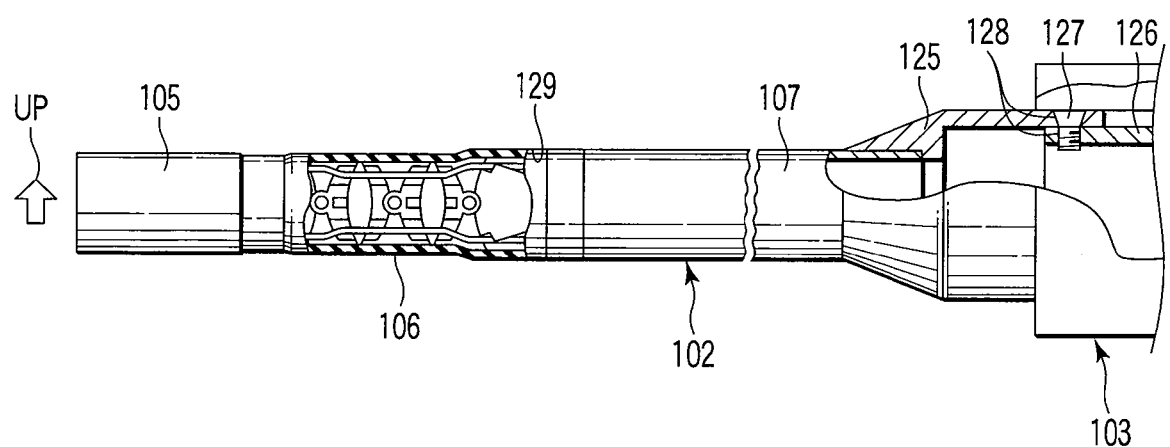
FIG. 7 is a side view schematically showing a portion of the operation part and the insertion part in the electronic endoscope shown in FIG. 5, the portion of the operation part and the insertion part being cut partially.

Next, a connecting configuration of the proximal end of the insertion part main body 107 of the insertion part 102 to the operation part 103 will be described with reference to FIG. 7.

A connection mouth piece 125 is fixed to the proximal end of the insertion part main body 107 of the insertion part 102 by a well known fixing element such as adhesive or the like. A portion of the operation part 103 to which the proximal end of the insertion part main body 107 of the insertion part 102 is connected is provided with a connection mouth piece receiving member 126.

The connection mouth piece 125 of the insertion part 102 is inserted into the receiving member 126 of the operation part 103, and then the connection mouth piece 125 is fixed to the receiving member 126 by a plurality of fixing elements 127 such as a plurality of screws.

A plurality of fixing element fixing holes 128 to which the plurality of fixing elements 127 are to be fixed are formed at a plurality of predetermined positions on each of the connection mouth piece 125 of the insertion part 102 and the receiving member 126 of the operation part 103.

Predetermined one of the fixing element fixing holes 128 is arranged at a position corresponding to a predetermined one of the predetermined bending directions of the bending portion 106 of the insertion part 102 operated by the first bending portion operation lever (the bending portion right and left operation lever, for example) 108*a* and second bending portion operation lever (the bending portion up and down operation lever, for example) 108*b* provided on the operation part 103, and that position corresponding to the predetermined one of the predetermined bending directions of the bending portion 106 is for example an upper position in a display contained in the not shown CCU (Camera Control Unit) connected to the CCU connector 111.

A predetermined mark is marked on a position adjoining the above described predetermined one fixing element fixing hole 128 on the connection mouth piece receiving member 126 of the operation part 103.

A predetermined mark 129 is marked at a position on the outer peripheral surface of the bending portion 106 of the insertion part 102, which corresponds to the predetermined one of the predetermined bending directions of the bending portion 106 of the insertion part 102 operated by the first bending portion operation lever (the bending portion right and left operation lever, for example) 108*a* and second bending portion operation lever (the bending portion up and down operation lever, for example) 108*b* provided on the operation part 103, and that position corresponding to the predetermined one of the predetermined bending directions of the bending portion 106 is for example the upper position in the display contained in the not shown CCU (Camera Control Unit) connected to the CCU connector 111.

When the insertion part 102 is connected to the operation part 103, the predetermined mark at the predetermined position on the outer peripheral surface of the bending portion 106 of the insertion part 102 is coincided with the predetermined mark adjoining the predetermined one of the plurality of fixing element fixing holes 128 of the receiving member 126 of the operation part 103 in the circumferential direction of the outer peripheral surface of the insertion portion 102.

By connecting the insertion part 102 to the operation part 103 as described above, when the bending portion 106 of the insertion part 102 is operated by the first bending portion operation lever (the bending portion right and left operation lever, for example) 108*a* and second bending portion operation lever (the bending portion up and down operation lever, for example) 108*b* provided on the operation part 103, the predetermined bending direction (for example, upper direction) of the bending portion 106 of the insertion part 102 and the predetermined direction (for example, upper direction) in the display contained in the not shown CCU (Camera Control Unit) connected to the CCU connector 111 can be surely coincided with each other.

Next, a configuration of a washing sheath 130 which is to be used in combination with the insertion part 102 of the endoscope 101 shown in FIG. 5 will be explained with reference to FIGS. 8A to 10.

The washing sheath 130 is used for washing out materials attached to the objective lens group 9*b* (referring to FIG. 1) for the imaging device 9*a* (referring to FIG. 1) and light projecting lens 8*a* (referring to FIG. 1) for the light guide members 8 (referring to FIG. 1) at the end surface of the tip portion 105 of the insertion part 102 of the endoscope 101 during an operation using the endoscope 101

Figure 8A:
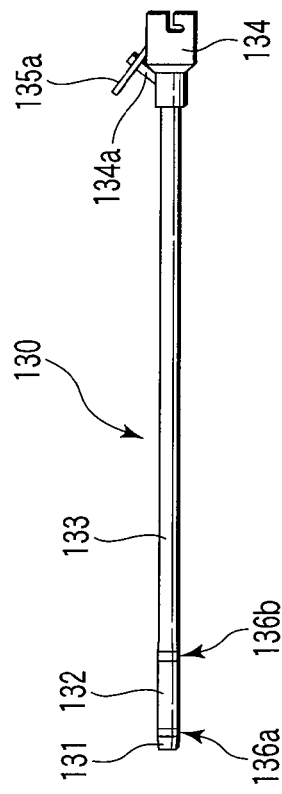
FIG. 8A is a side view schematically showing the whole of a washing sheath used in combination with the insertion part of the electronic endoscope shown in FIG. 5.
Figure 8B:
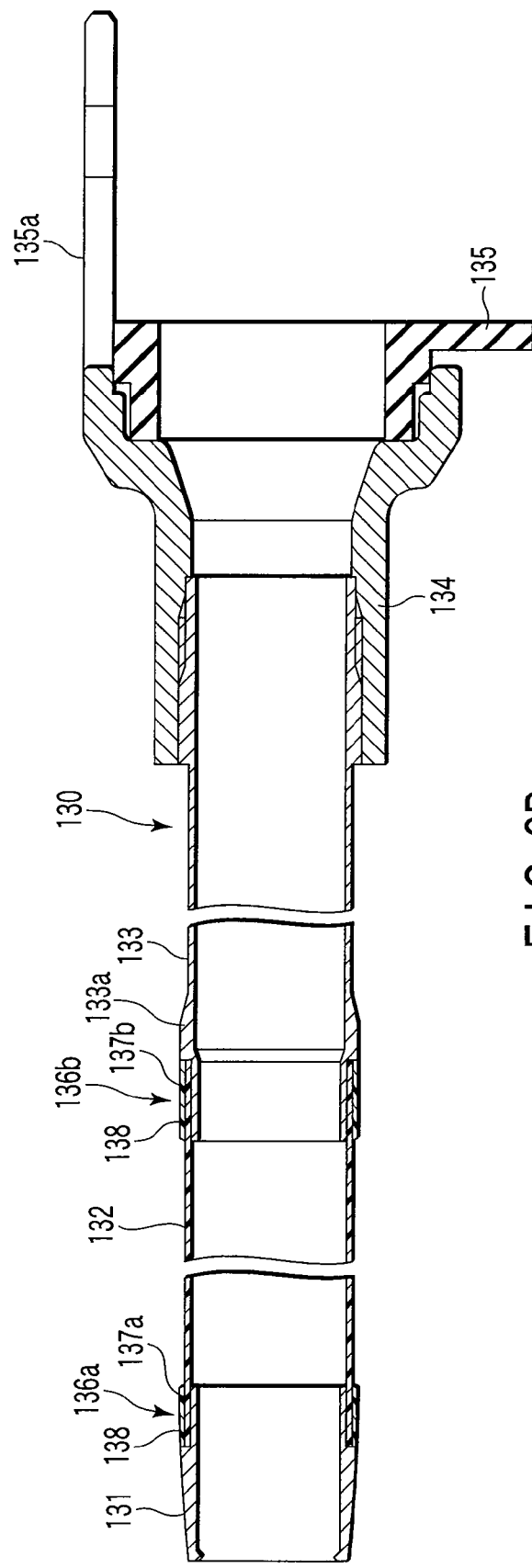
FIG. 8B is a schematic longitudinal sectional view of the washing sheath shown in FIG. 8A.
Figure 10:
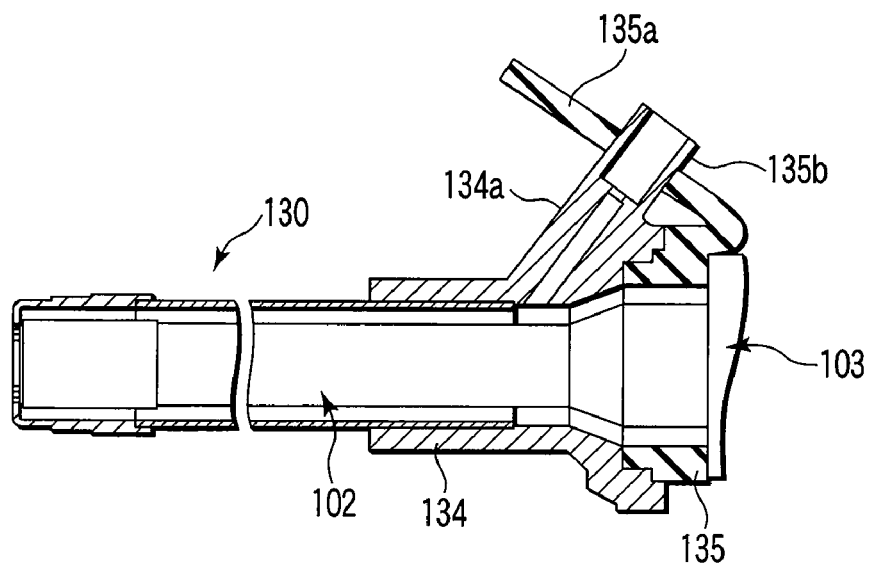
FIG. 10 is a schematic longitudinal sectional view, which is different from FIG. 8B, of the washing sheath shown in FIG. 8A.

The washing sheath 130 has a length being substantially the same as that of the insertion part 102 of the endoscope 101 and a inner diameter being slightly larger than the outer diameter of the insertion part 102 of the endoscope 101. And, as shown in FIGS. 8A and 8B, the washing sheath 130 comprises a tubular shaped tip member 131, a tubular shaped bending member 132, a tubular shaped main body member 133, a tubular shaped fitting mouth piece 134, and a seal member 135. As shown in FIGS. 8A and 10, a washing liquid introducing plug 134*a* projects from an outer peripheral surface of the fitting mouth piece 134.

The tip member 131, bending member 132, main body member 133, and fitting mouth piece 134 of the washing sheath 130 respectively correspond to the tip portion 105, bending portion 106, insertion part main body 107, and connection mouth piece 125 (referring to FIG. 7) of the insertion part 102 of the endoscope 101. Therefore, each of the tip part 131, the main body member 133, and the fitting mouth piece 134 may be made from hard material or flexible material, and the bending portion 106 is made from flexible material.

Both end portions of the bending portion 132 are fitted on an outer peripheral surface of a base end portion of the tip member 131 and an outer peripheral surface of an extending end portion of the main body member 133, and the both end portions of the bending portion 132 are fixed to the outer peripheral surface of the base end portion of the tip member 131 and the outer peripheral surface of the extending end portion of the main body member 133 by thread members 137*a*, 137*b* wound on the both end portions of the bending portion 132. The thread members 137*a*, 137*b* wound on the both end portions of the bending portion 132 are coated with thermosetting resin 138 including adhesive, so that thread wound fixing portions 136*a*, 136*b* are formed.

A portion 133*a* on an outer peripheral surface of the main body member 133, which adjoins an extending end portion of the outer peripheral surface of the main body member 133 corresponding to the thread wound fixing portion 136*b* and is located opposite to an extending end of the main body member 133, is configured to have a taper shape in which its diameter gradually increases with approaching to the extending end portion from a position being away from the extending end portion. An outer diameter of at a boundary between the adjoining portion 133*a* and the thread wound fixing portion 136*b* corresponding to the extending end portion is substantially set to the same as an outer diameter of the thread wound fixing portion 136*b*.

A tip portion on an outer peripheral surface of the tip member 131, which is located in a tip side of the base end portion of the tip member 131, is configured to have a taper shape in which its diameter gradually increases with approaching to the base end portion from a distal end. An outer diameter at a boundary between the tip portion and the thread wound fixing portion 136*a* corresponding to the base end portion is substantially set to the same as an outer diameter of the thread wound fixing portion 136*a*.

When the insertion part 102 of the endoscope 101 combined with the washing sheath 130 is used in a body cavity of a living thing, a trocar is set to the living thing to communicate the body cavity and the outer space, and the combination of the insertion part 102 of the endoscope 101 and the washing sheath 130 is inserted into and left from the body cavity through a hole of the trocar. A length of the trocar is shorter than that of the combination of the insertion part 102 of the endoscope 101 and the washing sheath 130.

Therefore, when the combination of the insertion part 102 of the endoscope 101 and the washing sheath 130 is inserted into the body cavity of the living thing, the taper shaped tip portion on the outer peripheral surface of the tip member 131 of the washing sheath 130 prevents the thread wound fixing portion 136a corresponding to the base end portion on the outer peripheral surface of the tip member 131 of the washing sheath 130 from hitting an outer end of the hole of the trocar. As a result, the insertion of the combination of the insertion part 102 of the endoscope 101 and the washing sheath 130 into the body cavity of the living thing through the hole of the trocar becomes easy, and it is possible to prevent the thread wound fixing portion 136a corresponding to the base end portion on the outer peripheral surface of the tip member 131 of the washing sheath 130 from being damaged by the hitting.

Further, when the combination of the insertion part 102 of the endoscope 101 and the washing sheath 130 is left from the body cavity of the living thing, the taper shaped adjoining portion 133a on the outer peripheral surface of the main body member 133 of the washing sheath 130 prevents the thread wound fixing portion 136b corresponding to the extending end portion on the outer peripheral surface of the main body member 133 of the washing sheath 130 from hitting an inner end of the hole of the trocar. As a result, the leaving of the combination of the insertion part 102 of the endoscope 101 and the washing sheath 130 from the body cavity of the living thing through the hole of the trocar becomes easy, and it is possible to prevent the thread wound fixing portion 136b corresponding to the extending end portion on the outer peripheral surface of the main body member 133 of the washing sheath 130 from being damaged by the hitting.

Figure 9:
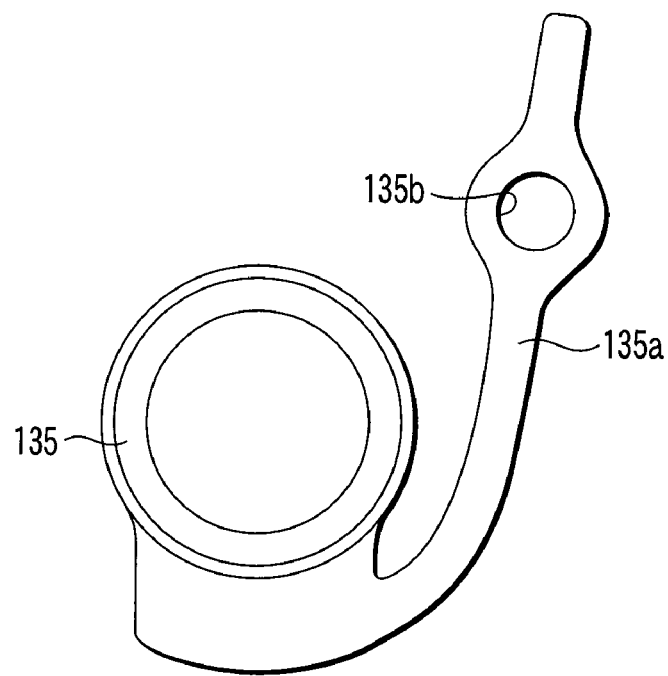
FIG. 9 is a front view schematically showing a seal member at the distal end of the washing sheath shown in FIGS. 8A and 8B.

As shown in FIG. 9, the seal member 135 of the washing sheath 130 is made of elastic material such as silicone rubber, and includes a strap 135a for easing the insertion and leaving of the insertion part 102 of the endoscope 101 (referring to FIG. 5) into and from the washing sheath 130 through a center hole of the seal member 135. The strap 135a has a fitting hole 135b.

While the seal member 135 of the washing sheath 130 is attached to the fitting mouth piece 134, as shown in FIGS. 8A and 10, the fitting hole 135b of the strap 135a is fitted on an outer peripheral surface of the washing liquid introducing plug 134a projecting from the outer peripheral surface of the fitting mouth piece 134. Therefore, as shown in FIG. 10, the strap 135a of the seal member 135 will not hamper the insertion and leaving of the insertion part 102 of the endoscope 101 (referring to FIG. 5) into and from the center hole of the seal member 135.

Next, a modification of the imaging unit used in the endoscope 101 shown in FIG. 5 will be explained with reference to FIGS. 11 to 16.

Figure 13:
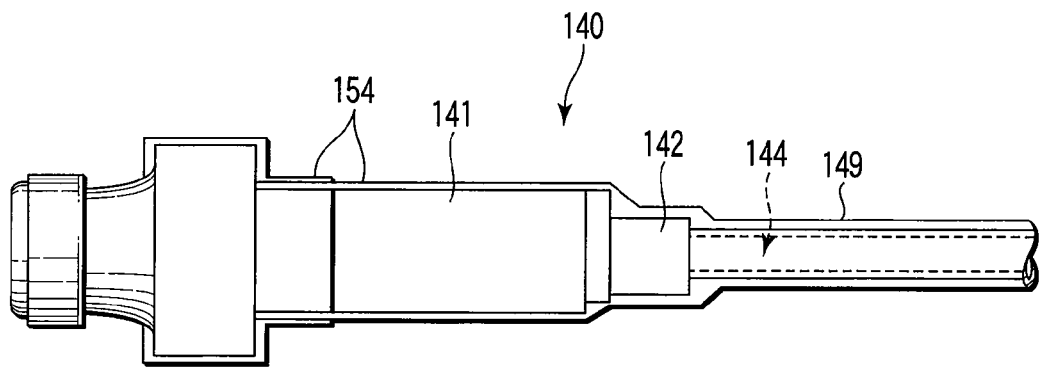
FIG. 13 is a schematic side view of the imaging unit shown in FIG. 11 with a heat shrinkable tube covering the outer surface of the imaging unit being cut away.
Figure 14:
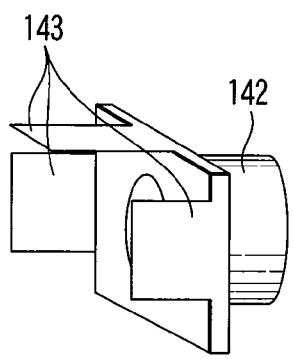
FIG. 14 is a schematic perspective view of a cover which is to be fitted on and fixed to a base end of a base end portion of a container accommodating an objective lens group and an imaging device in the imaging unit shown in FIG. 13.
Figure 15:
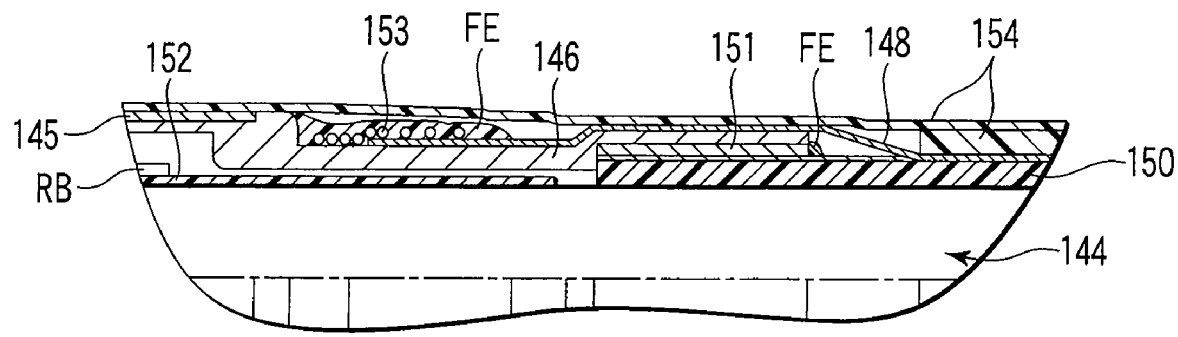
FIG. 15 is a larger enlarged schematic half sectional view of the other part of the signal cable of the imaging unit shown in FIG. 12, the other part being located in the operation part side of the relay circuit board.
Figure 16:
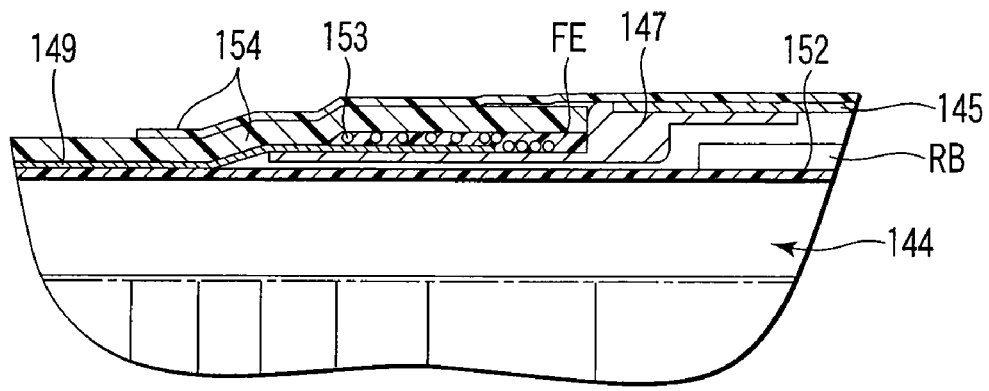
FIG. 16 is a larger enlarged schematic half sectional view of the part of the signal cable of the imaging unit shown in FIG. 11, the part being located in the distal end portion side of the relay circuit board.

As shown in FIG. 13, the imaging unit 140 comprises a container 141 accommodating the object lens group and the imaging device. A base end portion of the container 141 is configured to have a substantially square shape, and a cover 142 is fitted in an opening of an end of the base end portion. The cover 142 is fixed to the opening of the end of the base end portion of the container 141 by a well known fixing element such as adhesive. The cover 142 has three plates 143 fitted with the three surfaces of the square shaped inner periphery of the opening of the base end portion of the container 141.

Figure 11:
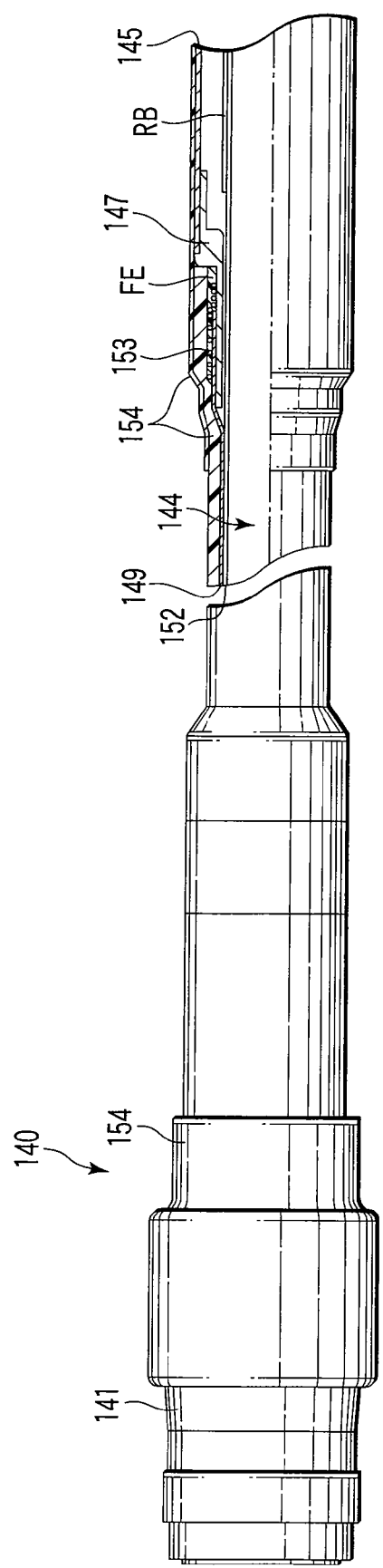
FIG. 11 is a side view schematically showing an imaging unit used in a modification of the electronic endoscope shown in FIG. 5, a part of a signal cable of the imaging unit, which is located in a distal end portion side of a relay circuit board, being cut.
Figure 12:
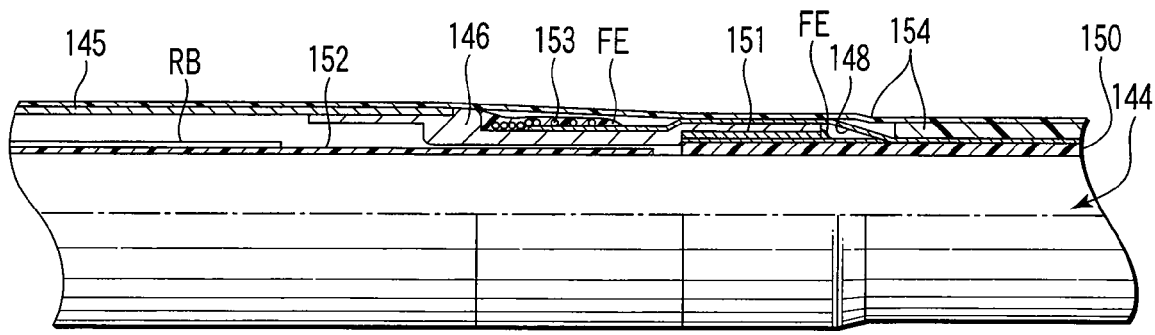
FIG. 12 is an enlarged schematic half sectional view of the other part of the signal cable of the imaging unit shown in FIG. 11, the other part being located in an operation part side of the relay circuit board.

A signal cable 144 extending from the various electric/electronic parts including the image device in the container 141 extends out through an opening of the cover 142. And, as shown in FIGS. 11 and 12, a relay board RB is connected to a position of the signal cable 144 which is located away from the container 141. The relay board RB generates a part of driving signals for the imaging device and makes electrical noise.

An outside of the relay board RB on the signal cable 144 in the diametrical direction of the signal cable 144 is covered by an electrical noise shielding member 145, and an operation part side (that is, a side being away from the container 141) and tip portion side (that is, a side being near to the container 141) of the relay board RB in the longitudinal direction of the signal cable 144 are covered by mouth pieces 146 and 147. The mouth piece 146 of the operation part side (that is, the side being away from the container 141) of the relay board RB is pressed on the signal cable 144 by a braid 148 of thin metal wires, and also the mouth piece 147 of the tip portion side (that is, the side being near to the container 141) of the relay board RB is pressed on the signal cable 144 by a braid 149 of thin metal wires.

The signal cable 144 is covered by a non-conductive outer shell er 150 and a braid 151 of metal wires. However, the non-conductive outer shell 150 and the braid 151 are removed from a portion of the outer peripheral surface of the signal cable 144 between the mouth piece 146 of the operation part side (that is, the side being away from the container 141) of the relay board RB and the container 141, and in place of them a heat shrinkable tube 152 is fitted on the above described portion of the outer peripheral surface of the signal cable 144. The heat shrinkable tube 152 prevents the twist of the plurality of signal lines of the signal cable 144 from coming loose in the above described portion of the outer peripheral surface of the signal cable 144 from which the non-conductive outer shell 150 and the braid 151 are removed. The relay board RB and the predetermined signal lines of the signal cable 144 are electrically connected with each other through an opening formed in the heat shrinkable tube 152.

The electrical noise shielding member 145 and the mouth pieces 146 and 147 covering the relay board RB on the outer peripheral surface of the signal cable 144 are electrically connected and fixed with each other by a well known electrical connection manner. Further, the mouth pieces 146 and 147 and the braids 148 and 149 corresponding thereto are electrically connected with each other by winding metal wires 153 such as for example Ni—Cr wires, Cu wires, or the like on end portions of the braids 148 and 149 covering the outer peripheral surfaces of the mouth pieces 146 and 147 and by fixing the windings of the metal wires 153 on the outer peripheral surfaces of the mouth pieces 146 and 147 with well known fixing elements FE.

The end portion of the braid 151 of the signal cable 144 adjoining the mouth piece 146 of the operation part side (that is, the side being away from the container 141) of the relay board RB is turned over and together with the end portion of the outer shell 150 adjoining the mouth piece 146 is inserted in the hole of the mouth piece 146. Finally, the end portion of the braid 151 is electrically connected with and fixed to the mouth piece 146 by a well known fixing element FE such as adhesive or solder or the like.

At least a part of the outer peripheral surface of the imaging unit 141, that part being located in the inner space of the insertion part 102 of the endoscope 101, is covered by a heat shrinkable tube 154 in a liquid tight manner.

Therefore, the end portions of the braids 148, 149 and metal wires 153 for the relay board RB, and the end portion of the braid 151 of the signal cable 144 must not be exposed in order to protect the heat shrinkable tube 154 from being broken. If necessary, the end portions of the braids 148, 149 and the metal wires 153 can be covered with annular members. Alternatively, the end portions of the braids 148, 149 can be fixed to the holes of the mouth pieces 146 and 147 by the above described well known fixing elements FE while the end portions of the braids 148, 149 are pushed into the holes of the mouth pieces 146 and 147 without using the metal wires 153.

While the endoscope 101 is sterilized by using an autoclave device, steam enters into the inner space of the endoscope 101. Therefore, the braid 151 of the metal wires for the signal cable 144 and the electrical noise shield member 145, mouth pieces 146, 147, and braids 148, 149 for the relay board RB are preferably made of stainless material which is very hard to be rusted in high temperature.

The conventional electrical connection manner for the electrical connection and fixation between the electrical noise shield member 145 and the mouth pieces 146, 147 for the relay board RB must surely maintain the above described electrical connection and fixation in highly pressured and highly heated conditions while the endoscope 101 is repeatedly sterilized by using the autoclave device. As such a conventional electrical connection manner, laser welding or soldering can be employed as examples. Similarly, the conventional fixing elements FE for fixations between the mouth pieces 146, 147 and braids 148, 149 for the relay board RB must surely maintain the above described fixation in highly pressured and highly heated conditions while the endoscope 101 is repeatedly sterilized by using the autoclave device. As such a conventional fixing element FE, soldering can be employed as an example. Further, the soldering can prevent the end portions of the braids 148, 149 and metallic wires 153 from exposing. Depending on a condition of high temperature and high pressure applying on the endoscope while the endoscope 101 is sterilized by using the autoclave device, adhesive can be used in place of the soldering.

When a stainless member is soldered, a flux is usually used to improve wetting of a solder to the stainless member. However, if the flux is sufficiently removed after a soldering is finished, the soldering is destroyed by the remaining flux in the highly pressured and highly heated condition while the endoscope 101 is sterilized by using the autoclave device. In this modification, the above described insufficient removing of the flux tend to be produced at the end portions of the braids 148, 149 covering the outer peripheral surfaces of the mouth pieces 146, 147. Therefore, in this modification, in place of using a flux, a portion of the stainless member to be soldered, specifically each of the end portions of the braids 148, 149 covering the outer peripheral surfaces of the mouth pieces 146, 147, is subjected to a surface treatment such as Ni plating to improve wetting of the solder.

Next, a check valve device and vent valve device of an endoscope, the endoscope according to another embodiment of the present invention and being applicable to a sterilization by using an autoclave device, will be explained with reference to FIGS. 17A to 18, and a vent valve device of an endoscope, the endoscope according to a further embodiment of the present invention and being applicable to a sterilization by using gas, will be explained with reference to FIGS. 19 to 21.

The autoclave device performs a sterilization by a high temperature under high pressure. Therefore, the endoscope being applicable to the sterilization by using the autoclave device must maintains the inner space of the endoscope and the outer space of the endoscope equally in pressure. To do so, the endoscope being applicable to the sterilization by using the autoclave device must keep to open the vent valve device for communicating the inner space of the endoscope with the outer space of the endoscope while the endoscope 101 is sterilized by using the autoclave device.

But, the endoscope being applicable to the sterilization by using gas must keep to close the vent valve device so that the gas will not enter the inner space of the endoscope while the endoscope 101 is sterilized by gas.

Each of a cap for autoclave sterilization and a cap for leak test can be fitted on the check valve device of the endoscope being applicable to the sterilization by using the autoclave device. The cap for autoclave sterilization has a function to keep opening of the check valve device. The cap for leak test has a function to keep opening of the vent valve device.

Each of a cap for gas sterilization and a cap for leak test can be fitted on the check valve device of the endoscope being applicable to the sterilization by using gas. The cap for gas sterilization has a function to keep closing of the vent valve device. The cap for leak test has a function to keep opening of the vent valve device.

The cap for autoclave sterilization must not be fitted on the vent valve device of the endoscope being applicable to the sterilization by using gas, and the cap for gas sterilization must not be fitted on the check valve device of the endoscope being applicable to the sterilization by using the autoclave device.

As shown in FIG. 17A, the check valve device 22 and vent valve device 23 of an endoscope being applicable to the sterilization by using the autoclave device are provided side by side on an extending end portion 21 of a universal cord 20 of the endoscope, and a not shown light guide connector projects from the extending end portion 21.

The check valve device 22 comprises a mouth piece main body 24 fixed to an outer wall of the extending end portion 21 by a nut 24b, and the mouth piece main body 24 has a communication hole 24a for communicating the inner space of the extending end portion 21 with the outer space thereof. An outer cylindrical member 25 is fitted on and fixed to an outer peripheral surface of an outer projecting part of the mouth piece main body 24, the outer projecting part projecting into the outer space. An annular gap is produced between a portion of the inner peripheral surface of the outer cylindrical member 25, the portion corresponding to the outer end portion of the outer peripheral surface of the outer projecting part of the mouth piece main body 24, and the outer end portion of the outer peripheral surface of the outer projecting part of the mouth piece main body 24. And, a cylindrical cam member 26 is fitted in the annular gap. A cam hole is formed in the peripheral wall of the cylindrical cam member 26. And, a cam pin 27 is fixed to the outer end portion of the outer peripheral surface of the outer projecting part of the mouth piece main body 24. And, the cam pin 27 of the mouth piece main body 24 is inserted into the cam hole of the cylindrical cam member 26.

Further, as shown in FIGS. 17A to 17C, a circular arc shaped groove 28a is formed in the outer end portion of the outer projecting part of the mouth piece main body 24, and the groove 28a is located outward from the cam pin 27 and extends in the circular direction of the outer end portion. A circular arc shaped groove 28b is further formed in the peripheral wall of the cam member 26, and the groove 28b is located outward from the cam hole and extends in the circular direction of the cam member 26. The circular arc shaped groove 28a of the mouth piece main body 24 is opened toward the outer space at the outer end of the mouth piece main body 24, and is arranged side by side with respect to the circular arc shaped groove 28b of the cam member 26 in a direction along the longitudinal center line of the mouth piece main body 24.

A diametrically enlarged inner hole 29 is formed in an axial center of the outer end portion of the outer projecting part of the mouth piece main body 24 by diametrically enlarging the through hole 24a. An inner cylindrical member 30 is accommodated in the enlarged inner hole 29. A valve seat 32 is formed in the inner peripheral surface of a center hole 31 of the inner cylindrical member 30, and the valve seat 32 faces outward in the direction along the longitudinal center line of the inner cylindrical member 30. A check valve member 33 is inserted in the center hole 31 of the inner cylindrical member 30, and the check valve member 33 can be movable between a seated or close position at which the check valve member 33 is seated on the valve seat 32 and a separated or open position at which the check valve member 33 is separated from the valve seat 32.

A pressure receiving member 34 is fixed to the inner end of the check valve member 33 projecting from the center hole 31 of the inner cylindrical member 30 into the enlarged inner hole 29 of the mouth piece main body 24, and the pressure receiving member 34 further functions as a spring stop. An urging spring 35 is wound around the outer peripheral surface of the check valve member 33 between the inner end of the inner cylindrical member 30 and the pressure receiving member 34 as the spring stop at the inner end of the check valve member 33, and the urging spring 35 is compressed between them to urge the check valve member 33 onto the valve seat 32 on the inner peripheral surface of the center hole 31 of the inner cylindrical member 30.

An engaging pin 36 is fixed to the outer peripheral surface of the outer cylindrical member 25, and the engaging pin 36 projects outward in the diametrical direction of the outer cylindrical member 25.

In check valve device 22 configured as described above, usually the check valve member 33 is pressed onto the valve seat 32 on the inner peripheral surface of the center hole 31 of the inner cylindrical member 30 by the urging force of the urging spring 35 so that the check valve device 22 is closed. That is, the communication between the inner space of the endoscope and the outer space of the endoscope through the check valve device 22 is stopped. However, when the pressure in the inner space of the endoscope becomes higher than that in the outer space and the pressure received by the pressure receiving member 34 at the inner end of the check valve member 33 becomes larger than the urging force of the urging spring 35, the check valve member 33 leaves from the valve seat 32 on the inner peripheral surface of the center hole 31 of the inner cylindrical member 30 against the urging force of the urging spring 35 so that the check valve device 22 is opened. That is, the high pressure of the inner space of the endoscope is lowered to the pressure of the outer space.

As shown in FIG. 17A, the vent valve device 23 comprised a cylindrical valve seat member 37 fixed to the extending end portion 21 of the universal code 20 of the endoscope so that the cylindrical valve seat member 37 adjoin the mouth piece main body 24 of the check valve device 22. An inner hole 38 of the valve seat member 37 communicates with the inner space of the extending end portion 21 and the outer space.

A valve seat 39 is formed at a position near to the outer end of the inner hole 38 on the inner peripheral surface of the inner hole 38 of the valve seat member 37, and the valve seat 39 faces inward in a direction along the longitudinal center line of the inner hole 38. A valve member 40 is inserted in the inner hole 38 of the valve seat member 37, and the valve member 40 can be movable between a seated or close position at which the valve member 40 is seated on the valve seat 39 and a separated or open position at which the valve member 40 is separated from the valve seat 39.

An annular spring stopper 41a is fixed at an inner end adjoining position on the inner hole 38 of the valve seat member 37. An urging spring 41 is wound around the outer peripheral surface of the valve member 40 between the annular spring stopper 41a and a position on the outer peripheral surface of the valve member 40, the position being located inward from the valve seat abutting portion on the outer peripheral surface of the valve member 40. And, as shown in FIG. 17A, the valve member 40 is pressed on the valve seat 39 by the urging force of the urging spring 41. That is, the communication between the inner space of the endoscope and the outer space of the endoscope through the inner hole 38 of the valve seat member 37 is stopped.

The valve member 40 includes an outer projecting portion 40a projecting outward from the extending end portion 21 of the universal cord 20 while the valve member 40 is located in the above described close position.

Figure 18:
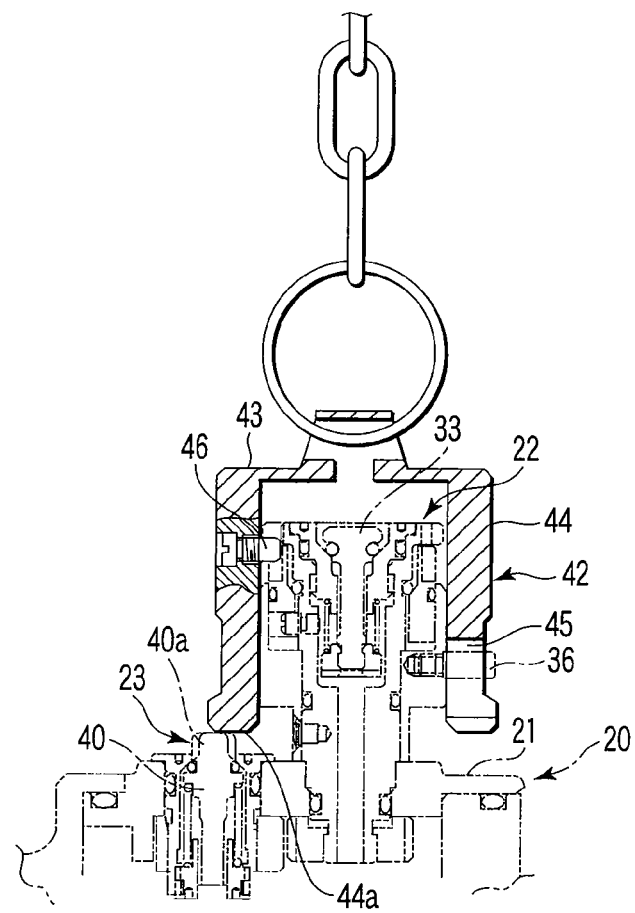
FIG. 18 is a longitudinal sectional view schematically showing a cap for autoclave sterilization used for the check valve device of FIG. 17A, the cap for autoclave sterilization being mounted on the check valve device.

FIG. 18 shows the cap 42 for autoclave sterilization, fitted on the check valve device 22.

The cap 42 for autoclave sterilization comprises a cylindrical cap body 44 including a head 43 detachably fitted on a part of the check valve device 22 which projects outward from the extending end portion 21 of the universal cord 20. A bottom of the cap body 44 is configured as an abutting portion 44a to be in contact with the outer end of the outer projecting portion 40a of the valve member 40 of the vent valve device 23 which adjoins the check valve device 22 on the extending end portion 21 of the universal cord 20. A cut out 45 is formed in the bottom to fit on the engaging pin 36 of the outer cylindrical member 25 of the check valve device 22.

A projection 46 is provided at a position near to the head 43 on the inner peripheral surface of the cap body 44.

The fitting of the cap 42 for autoclave sterilization on the check valve device 22 is possible only in a condition that the projection 46 on the inner peripheral surface of the cap body 44 is faced the circular arc shaped groove 28a on the outer projecting part of the mouth piece main body 24 and the circular arc shaped groove 28b in the cam member 26 and the outer end of the cut out 45 of the bottom of the cap body 44 is faced the engaging pin 36 of the outer cylindrical member 25 of the check valve device 22.

While the cap 42 for autoclave sterilization is fitted on the check valve device 22, the cap 42 for autoclave sterilization with the projection 46 can be rotational to the check valve device 22 within a range of a circumferential direction length (in this embodiment, a rotational angle of substantially 45 degrees) of each of the circular arc shaped groove 28a on the outer projecting part of the mouth piece main body 24 and the circular arc shaped groove 28b in the cam member 26.

While the cap 42 for autoclave sterilization is fitted on the check valve device 22, the cap 42 for autoclave sterilization with the projection 46 can be moved to the check valve device 22 within a range of a total of the width of the circular arc shaped groove 28a on the outer projecting part of the mouth piece main body 24 of the check valve device 22 and the width of the circular arc shaped groove 28b in the cam member 26 in the direction along the longitudinal center line of the mouth piece main body 24 of the check valve device 22.

When the cap 42 for autoclave sterilization is pressed inward to the extending end portion 21 of the universal cord 20 while the cap 42 for autoclave sterilization is fitted on the check valve device 22, the abutting portion 44a of the bottom of the cap 42 for autoclave sterilization presses the outer projecting portion 40a of the valve member 40 of the vent valve 23 inward to the extending end portion 22 of the universal cord 20. As a result, the valve member 40 of the vent valve 23 leaves from the valve seat 39 against the urging force of the urging spring 41. That is, the communication between the inner space of the endoscope and the outer space of the endoscope through the inner hole 38 of the valve seat member 37 is performed in the vent valve device 23, so that the pressure of the inner space of the endoscope and the pressure of the outer space of the endoscope are coincided with each other.

In this state, when the cap 42 for autoclave sterilization is rotated in a predetermined circular direction with respect to the check valve device 22 over the range of the circumferential direction length of the circular arc shaped groove 28a on the outer projecting part of the mouth piece main body 24 of the check valve device 22 (in this embodiment, to a rotational angle of substantially 90 degrees), the projection 46 of the cap 42 for autoclave sterilization pushes an end of the circular arc shaped groove 28b in the cam member 26 in the above described predetermined circular direction. As a result, the cam member 26 rotates on the outer peripheral surface of the outer projecting part of the mouth piece main body 24 in the predetermined circular direction with respect to the outer projecting part.

Such a relative rotation of the cam member 26 in the predetermined circumferential direction causes the cam member 26 to move inward with respect to the extending portion 21 of the universal cord 20 on the outer peripheral surface of the outer projecting part of the mouth piece main body 24 by the action of the cam hole in the peripheral wall of the cam member 26 to the cam pin 27 on the outer peripheral surface of the outer projecting part of the mouth piece main body 24.

Such an inward movement of the cam member 26 produces a gap between the outer end of the cam member 26 and the outer peripheral surface of the outer projecting part of the mouth piece main body 24. Since a not shown through hole is formed in a region of the outer peripheral surface of the outer projecting part of the mouth piece main body 24, the region facing the inner peripheral surface of the cam member 26, and the not shown through hole communicates with inner hole 29 of the mouth piece main body 24, the communication between the inner space of the extending end portion of the universal cord 20 (that is, the inner space of the endoscope) and the outer space is further performed through the gap and the not shown through hole. That is, also in the check valve device 22, the pressure of the inner space of the endoscope and the pressure of the outer space can be coincided with each other.

The cap for leak test, which is to be used for testing whether the inner space of the endoscope leaks to the outer space or not, is not shown, but it is configured by deleting the abutting portion 44a of the bottom of the cap body 44 from the above described cap 42 for autoclave sterilization and by providing the projection 46 at a position near to the head 43 on the inner peripheral surface of the cap body 44, the position being separated from the position near to the head 43 on the inner peripheral surface of the cap body 44 in the above described cap 42 for autoclave sterilization by 180 degrees in the circumferential direction of the inner peripheral surface.

As shown in FIGS. 17A to 17C, a cut out for a leak test cap KK1 is formed in the outer end portion of the outer projecting part of the mouth piece main body 24 of the check valve device 22, and the cut out for a leak test cap KK1 is located opposite to the above described circular arc shaped groove 28a on the mouth piece main body 24 in the diametrical direction of the mouth piece main body 24. Further, a cut out for a leak test cap KK2 is formed in the peripheral wall of the cam member 26, and the cut out for a leak test cap KK2 is located opposite to the above described circular arc shaped groove 28b in the peripheral wall of the cam member 26 in the diametrical direction of the cam member 26.

The cut outs for a leak test cap KK1, KK2 and the engaging pin 36 of the outer cylindrical member 25 are arrange at the same position in the circumferential direction of the outer cylindrical member 25.

The cut out for a leak test cap KK1 of the mouth piece main body 24 is opened to the outer space at the outer end of the mouth piece main body 24 and overlaps with the cut out for a leak test cap KK2 of the cam member 26 in the direction along the longitudinal center line of the mouth piece main body 24. Each of the size of the cut out for a leak test cap KK1 of the mouth piece main body 24 in the circumferential direction of the mouth piece main body 24 and the size of the cut out for a leak test cap KK2 of the cam member 26 in the circumferential direction of the cam member 26 is slightly larger than the size of the projection 46 in the circumferential direction of the inner peripheral surface of the cap main body 44, the projection 46 being located near to the head 43 on the inner peripheral surface of the cap main body 44.

The fitting of the cap for leak test on the check valve device 22 is possible only in a condition that the projection 46 on the inner peripheral surface of the cap main body 44 faces the cut out for a leak test cap KK1 of the outer projecting part of the mouth piece main body 24 and the cut out for a leak test cap KK2 of the cam member 26 and the outer end of the cut out 45 of the bottom of the cap main body 44 faces the engaging pin 36 on the outer cylindrical member 25 of the check valve device 22.

When the cap for leak test is fitted on the check valve device 22 and the cap for leak test is rotated in a predetermined circumferential direction with respect to the outer extending part of the mouth piece main body 24 of the check valve device 22 (in this embodiment, to the rotation angle of substantially 90 degrees), the projection 46 of the cap for leak test presses the cut out for a leak test cap KK2 of the cam member 26 in the predetermined circumferential direction so that the cam member 26 is rotated on the outer peripheral surface of the outer extending part of the mouth piece main body 24 in the predetermined circumferential direction with respect to the outer projecting part of the mouth piece main body 24.

Such a relative rotation of the cam member 26 in the predetermined circumferential direction causes the cam member 26 to move inward with respect to the extending portion 21 of the universal cord 20 on the outer peripheral surface of the outer projecting part of the mouth piece main body 24 by the action of the cam hole in the peripheral wall of the cam member 26 to the cam pin 27 on the outer peripheral surface of the outer projecting part of the mouth piece main body 24.

Such an inward movement of the cam member 26 produces the gap between the outer end of the cam member 26 and the outer peripheral surface of the outer projecting part of the mouth piece main body 24. Since the not shown through hole is formed in the region of the outer peripheral surface of the outer projecting portion of the mouth piece main body 24, the region facing the inner peripheral surface of the cam member 26, and the not shown through hole communicates with inner hole 29 of the mouth piece main body 24, the communication between the inner space of the extending end portion 21 of the universal cord 20 (that is, the inner space of the endoscope) and the outer space is performed through the gap and the not shown through hole. That is, it is possible to supply air into the inner space of the endoscope through the check valve device 22 so as to perform a test for leak of the inner space.

Figure 19:
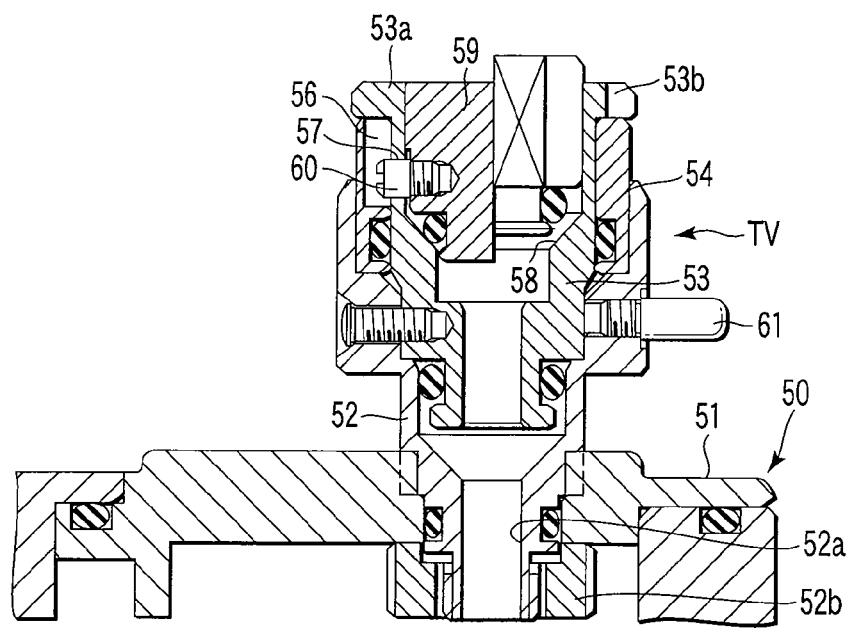
FIG. 19 is a longitudinal sectional view schematically showing a vent valve device of an endoscope which can be sterilized by gas and which is according to still another embodiment of the invention, in the left half of which a vent valve member is arranged in its closed position and in the right half of which the vent valve member is arranged in its opening position.

As shown in FIG. 19, the vent valve device TV of the endoscope, the endoscope according to the further embodiment of the present invention and being applicable to the sterilization by using gas, is provided on an extending end portion 51 of a universal cord 50 of the endoscope, and a not shown light guide connector projects from the extending end portion 51.

The vent valve device TV comprises a mouth piece main body 52 fixed to an outer wall of the extending end portion 51 by a nut 52b, and the mouth piece main body 52 has a communication hole 52a for communicating the inner space of the extending end portion 51 with the outer space thereof. An inner cylindrical member 53 is fitted in and fixed to an outer projecting part of the communication hole 52a of the mouth piece main body 52, the outer projecting part being located in a part of the mouth piece main body 52 projecting into the outer space.

An annular gap is produced between a portion of the inner peripheral surface of the communicating hole 52a of the mouth piece main body 52, the portion corresponding to the outer end portion of the outer peripheral surface of the inner cylindrical member 53, and the outer end portion of the outer peripheral surface of the inner cylindrical member 53. And, a cylindrical circumferentially slidable member 54 is fitted in the annular gap, and the circumferentially slidable member 54 can slide in the circumferential direction of the gap.

Further, as shown in FIG. 21, a longitudinal groove 55 is formed in the outer peripheral surface of the circumferentially slidable member 54. The longitudinal groove 55 is located outward from the outer end of the mouth piece main body 52 and extends inward from the outer end of the slidable member 54 in the longitudinal direction of the slidable member 54. The longitudinal groove 55 opens at the outer end of the slidable member 54.

A cam pin engaging groove 56 is formed in the inner peripheral surface of the slidable member 54, and the cam pin engaging groove 56 extends inward from the outer end of the slidable member 54 in the longitudinal direction of the slidable member 54.

As shown in FIG. 20A, a cam groove 57 is formed in the outer peripheral surface of the inner cylindrical member 53.

As shown in FIGS. 20B and 21, the inner cylindrical member 53 has an outer flange 53a at a position outward from the longitudinal outer end of the slidable member 54 and the outer flange 53a expand outward in the radial direction of the inner cylindrical member 53. A cut out 53b is formed at a predetermined position in the outer flange 53a of the inner cylindrical member 53.

Outwardly projecting engaging pin 61 is fixed to the outer peripheral surface of the mouth piece main body 52. The cut out 53b of the outer flange 53a of the inner cylindrical member 53 and the engaging pin 61 of the mouth piece main body 52 are located in the same position in the circumferential direction of the mouth piece main body 52.

A valve seat 58 is formed in the inner hole of the inner cylindrical member 53, and the valve seat 58 faces outward in the longitudinal direction of the inner cylindrical member 53. A valve member 59 is accommodated in the inner hole of the inner cylindrical member 53 so as to be movable between a close position at which the valve member 59 is seated on the valve seat 58 and an open position at which the valve member 59 is separated from the valve seat 58. A cam pin 60 is provided on and projects out from the outer peripheral surface of the valve member 59. The cam pin 60 passes through the cam groove 57 of the inner cylindrical member 53 and projects into the cam pin engaging groove 56 of the slidable member 54.

As shown in a left half of FIG. 21, while the longitudinal groove 55 of the slidable member 54 coincides with the cut out 53b of the outer flange 53a of the inner cylindrical member 53 in the circumferential directional of the inner cylindrical member 53, the valve member 59, the cam pin 60 of which is passed through the cam pin engaging groove 56 of the slidable member 54, is seated on the valve seat 58 of the inner cylindrical member 53. That is, the vent valve device VT is closed.

The maximum diameter of the outer projecting part of the vent valve TV for the endoscope being applicable to the sterilization by using gas (In the above described further embodiment, the diameter of the outer end portion of the outer projecting part of the mouth piece main body 52) is smaller than the maximum diameter of the outer projecting part of the check valve device 22 for the endoscope being applicable to the sterilization by using an autoclave device and described above with reference to FIGS. 17A to 18 (In the above described embodiment, the diameter of the outer cylindrical member 25).

As a result, each of a cap for gas sterilization and a cap for leak test, both of which can be fitted on the outer projecting part of the vent valve device VT and will be explained in detail in the following, can not be fitted on the outer projecting part of the check valve device 22 for the endoscope being applicable to the sterilization by using an autoclave device.

FIG. 21 shows the cap for gas sterilization 62 fitted on the outer projecting part of the vent valve device VT. The main configuration of the cap for gas sterilization 62 and that of the cap for leak test, both used for the endoscope being applicable to the sterilization by using gas, are the same as to each other. Therefore, the configuration of the cap for gas sterilization 62 will be explained with reference to FIG. 21.

The configuration of the cap for gas sterilization 62 is substantially the same as that of the cap for leak test to be fitted on the check valve device 22 for the endoscope being applicable to the sterilization by using an autoclave device, excluding their sizes, the cap for leak test being describe above with reference to FIGS. 17A to 18.

The cap 62 for gas sterilization comprises a cylindrical cap body 62a including a head detachably fitted on a part of the vent valve device TV which projects outward from the extending end portion 51 of the universal cord 50. A cut out 62b is formed in the bottom of the cap 62 for gas sterilization to fit on the engaging pin 61 of the mouth piece main body 52 of the vent valve device TV. The cut out longitudinally extends along the longitudinal center line of the mouth piece main body 52, and the size of the cut out in the circumferential direction of the mouth piece main body 52 is only slightly larger than the diameter of the engaging pin 61.

A projection 63 is provided at a position near to the head on the inner peripheral surface of the cap body 62a.

The fitting of the cap 62 for gas sterilization on the vent valve device TV is possible only in a condition that the projection 63 on the inner peripheral surface of the cap body 62a is faced the cut out 53b of the outer flange 53a of the inner cylindrical member 53 and the outer end of the longitudinal groove 55 of the slidable member 54 and the outer end of the cut out 62b of the bottom of the cap body 62a faces the engaging pin 61 of the mouth piece main body 52 of the vent valve device TV.

There is no cut out other than the cut out 53b in the outer flange 53a of the inner cylindrical member 53 of the vent valve device TV, and the cut out 53b of the outer flange 53a of the inner cylindrical member 53 coincides with the engaging pin 61 of the mouth piece main body 52 of the vent valve device TV in the circumferential direction of the inner cylindrical member 53.

In contrast thereto, when the cap for autoclave sterilization 42 is fitted on the outer projecting part of the check valve device 22 of the endoscope being applicable to the sterilization by using an autoclave device, the circular arc shaped groove 28a in the outer projecting part of the mouth piece main body 24 of the check valve device 22 and the circular arc shaped groove 28b in the cam member 26, both being located in the direction along the longitudinal center line of the mouth piece main body 24 of the check valve device 22 and being to be fitted on the projection 46 on the inner peripheral surface of the cap for autoclave sterilization 42, are located in a position opposite to the projection 36 on the outer peripheral surface in the circumferential direction of the outer circumferential surface of the mouth piece main body 24 (in this further embodiment, in the diametrical direction of the mouth piece main body 24).

Therefore, when the cap for autoclave sterilization 42 is tried to fit on the outer projecting part of the vent valve device TV in a condition that the cut out 45 of the bottom faces the engaging pin 61 of the mouth piece main body 52 of the vent valve device TV, the projection 46 on the inner peripheral surface of the cap main body 44 of the cap for autoclave sterilization 42 abuts a position on the outer flange 53a of the inner cylindrical member 53 of the outer projecting part of the vent valve device TV, the position being located opposite to the cut out 53b in the circumferential direction of the inner cylindrical member 53, so that the projection 46 will not enter into the cut out 53b.

As a result, the cap for autoclave sterilization 42 can be placed a little on the outer projecting part of the vent valve device TV, but the cap for autoclave sterilization 42 can not be fully fitted on the outer projecting part of the vent valve device TV in its right position to operate the vent valve device TV.

By inserting the projection 63 on the inner peripheral surface of the cap main body 62a of the cap for gas sterilization 62 into the longitudinal groove 55 of the slidable member 54 through the cut out 53b of the outer flange 53a of the inner cylindrical member 53 of the vent valve device TV, and at the same time by fitting the cut out 62b of the bottom of the cap main body 62a on the engaging pin 61 of the mouth piece main body 52 of the vent valve device TV, the cap for gas sterilization 62 can be fully fitted on the outer projecting part of the vent valve device TV in its right position.

In this condition, as shown in FIG. 21, the valve member 59 with its cam pin 60 inserting into the cam pin engaging groove 56 seats on the valve seat 58 of the inner cylindrical member 53. That is, the vent valve device TV is closed. And, the longitudinal cut out 62b in the bottom of the cap main body 62a fitted on the engaging pin 61 of the mouth piece main body 52 of the vent valve device TV prevents the rotation of the cap for gas sterilization 62 on the outer projecting part of the vent valve device TV. That is, the cap for gas sterilization 62 prevents the opening of the vent valve device TV.

Therefore, when the endoscope being applicable to the sterilization by using gas is sterilized by using gas while the cap for gas sterilization 62 is fully fitted on the outer projecting part of the vent valve device TV in its right position, the gas for sterilization will not enter into the inner space of the endoscope through the vent valve device TV.

The configuration of the cap for leak test to be fitted on the vent valve device TV is different from the cap for gas sterilization described above with reference to FIG. 21 in that the inner end of the longitudinal cut out 62b of the bottom of the cap main body 62a extends in a predetermined direction along the circumferential direction of the cap main body 62a by a predetermined distance (for example, the rotational angular distance of 90 degrees in the anti-clockwise direction viewing downward from a position above the cap main body 62a). Owing to this circularly extending portion of the inner end of the cut out 62b, the cap for leak test fully fitted on the outer projecting part of the vent valve device TV in its right position can further rotates with respect to the outer projecting part of the vent valve device TV in a circumferential direction opposing to the predetermined extending direction of the inner end of the cut out 62b by the predetermined distance (for example, the rotational angular distance of 90 degrees in the clockwise direction viewing downward from the position above the cap main body 62a).

Such a rotation of the cap for leak test causes the slidable member 54 having the longitudinal groove 55 into which the projection 63 on the inner peripheral surface of the cap main body 62a is inserted to rotate in the circumferential direction opposing to the predetermined extending direction of the inner end of the cut out 62b by the predetermined distance, and further the cam pin 60 is moved by the action of the cam pin engaging groove 56 in the circumferential direction opposing to the predetermined extending direction of the inner end of the cut out 62b by the predetermined distance. Since the cam pin 60 is passed through the cam groove 57 of the inner cylindrical member 53 and is fixed to the valve body 59, the cam pin 60 is moved outward along the longitudinal center line of the inner cylindrical member 53 by a predetermined distance by the action of the cam groove 57 of the inner cylindrical member 53 while the cam pin 60 is moved in the circumferential direction opposing to the predetermined extending direction by the predetermined distance. As a result, the valve member 59 separates from the valve seat 58 in the inner hole of the inner cylindrical member 53 as shown in a right half of FIG. 21. That is, the vent valve device TV is opened.

While the vent valve device TV is opened by the cap for leak test, it is possible to supply air into the inner space of the endoscope through the vent valve device TV so as to perform a test for leak of the inner space.

As shown in the following table 1, the cap for autoclave sterilization 42 and the cap for leak test can be fitted on the check valve device 22 of the endoscope being applicable to the sterilization by using an autoclave device, but the cap for gas sterilization 62 can not be fitted on the check valve device 22. And, the cap for gas sterilization 62 and the cap for leak test can be fitted on the vent valve device TV of the endoscope being applicable to the sterilization by using gas, but the cap for autoclave sterilization 42 can not be fitted on the vent valve device TV.

TABLE 1

|  | Check valve device of autoclave sterilization applicable endoscope | Vent valve device of gas sterilization applicable endoscope |
| --- | --- | --- |
| Cap for autoclave sterilization | ○ | X |
| Cap for gas sterilization | X | ○ |
| Cap for leak test | ○ | ○ |

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bending portion of an elongate insertion part of an endoscope, the endoscope including an operation part configured for operating the elongate insertion part, the elongate insertion part including a proximal end and a distal end and adapted to be inserted into an inner space of an object, with the distal end as a leading end, and the operation part of the endoscope being connected to the proximal end of the elongate insertion part, and the elongate insertion part including an insertion part main body which has the proximal end, which extends toward the distal end and which has an extending end area proximate to the distal end, a tip portion which has the distal end and which has a base end area, and the bending portion which is arranged between the extending end area of the insertion part main body and the base end area of the tip portion and which has one end area connected to the extending end area of the insertion main body and the other end area connected to the base end area of the tip portion, and the bending portion together with the tip portion being bendable by being operated with the operation part, the bending portion comprising:

a bending structure including first and second portions which correspond to the one end area and the other end area of the bending portion, the first portion and second portion overlapping the extending end area of the insertion part main body and the base end area of the tip portion;

a first fixing member fixing the first portion of the bending structure to the extending end area of the insertion part main body overlapped with the first portion, and having a head exposed on an outer surface of the first portion;

a second fixing member fixing the second portion of the bending structure to the base end area of the tip portion overlapped with the second portion, and having a head exposed on an outer surface of the second portion;

a flexible cover member which covers the bending structure from the first portion to the second portion, which also covers the heads of the first and second fixing members, and which has one end and the other end portion corresponding to the first and second portion of the bending structure;

thread members wound on the one and the other end portions of the cover member, and making up winding portions on the one and the other end portions; and resin layers covering the winding portions of the thread members wound on the one and the other end portions of the cover member, wherein each thread member has a winding start portion and a winding end portion both which are arranged between each of the one and the other end portions of the cover member and the winding portion thereon, and both of which extend substantially parallel to one another in a longitudinal direction of the insertion part, and the winding start portion and winding end portion on each of the one and the other end portions of the cover member are separated from the head of the fixing member corresponding thereto in a circumferential direction of each of the one and the other end portion of the cover member and are separated from each other in the circumferential direction.

2. The bending portion according to claim 1, wherein each said fixing member includes a screw having the head.

3. The bending portion according to claim 1, wherein the head of each said fixing member is arranged at a substantially middle position between the winding start portion and the winding end portion of the thread member in the circumferential direction of the cover member.

4. An endoscope comprising:

an insertion part including a proximal end and a distal end and adapted to be inserted into an inner space of an object, with the distal end as a leading end, and an operation part connected to the proximal end of the insertion part and operating the insertion part, the insertion part including an insertion part main body which has the proximal end, which extends toward the distal end and which has an extending end area proximate to the distal end, a tip portion which has the distal end and which has a base end area near to the extending end area of the insertion part main body, and a bending portion which is arranged between the extending end area of the insertion part main body and the base end area of the tip portion and which has one end area connected to the extending end area of the insertion part main body and the other end area connected to the base end area of the tip portion, the bending portion together with the tip portion being bendable by being operated with the operation part, and the bending portion of claim 1.

* * * * *